(12) United States Patent
Sugiura

(10) Patent No.: US 6,557,554 B1
(45) Date of Patent: May 6, 2003

(54) HIGH-FREQUENCY OSCILLATION ARTIFICIAL RESPIRATION APPARATUS

(75) Inventor: Yasuhito Sugiura, Shizuoka (JP)

(73) Assignee: Suzuki Motor Corporation, Shizuoka (JP)

( * ) Notice: Subject to any disclaimer, the term of this patent is extended or adjusted under 35 U.S.C. 154(b) by 244 days.

(21) Appl. No.: 09/690,848

(22) Filed: Oct. 18, 2000

(30) Foreign Application Priority Data

Oct. 29, 1999 (JP) ............................................ 11-309447
Dec. 22, 1999 (JP) ............................................ 11-363696

(51) Int. Cl.$^7$ ............................................ A61M 16/00
(52) U.S. Cl. ............................. 128/204.18; 128/204.21
(58) Field of Search ....................... 128/204.18, 204.21, 128/204.24, 204.25

(56) References Cited

U.S. PATENT DOCUMENTS

| | | | | |
|---|---|---|---|---|
| 4,463,756 A | * | 8/1984 | Thuc | 128/204.21 |
| 4,747,403 A | * | 5/1988 | Gluck et al. | 128/204.21 |
| 4,788,974 A | * | 12/1988 | Phuc | 128/204.21 |
| 4,805,612 A | * | 2/1989 | Jensen | 128/204.21 |
| 5,555,880 A | * | 9/1996 | Winter et al. | 128/204.21 |
| 5,850,835 A | | 12/1998 | Takaki et al. | |
| 6,257,234 B1 | * | 7/2001 | Sun | 128/204.18 |
| 6,415,791 B1 | * | 7/2002 | Van Brunt | 128/200.24 |
| 6,435,182 B1 | * | 8/2002 | Lutchen et al. | 128/200.24 |
| 6,446,629 B1 | * | 9/2002 | Takaki et al. | 128/204.18 |

FOREIGN PATENT DOCUMENTS

| | | |
|---|---|---|
| JP | 2-7569 | 1/1990 |
| JP | 2798255 | 7/1998 |
| JP | 2798256 | 7/1998 |
| JP | 2798257 | 7/1998 |

OTHER PUBLICATIONS

An English Language abstract of JP 2–798255.
An English Language abstract of JP 2–798256.
An English Language abstract of JP 2–798257.

* cited by examiner

Primary Examiner—Weilun Lo
Assistant Examiner—Mital Patel
(74) Attorney, Agent, or Firm—Greenblum & Bernstein, P.L.C.

(57) ABSTRACT

The present invention provides a high-frequency oscillation artificial respiration apparatus that includes an inhale gas introducer that supplies an inhale gas containing oxygen to a patient and a patient side path that guides the inhale gas from the inhale gas introducer into the patient. An oscillating air pressure provider that applies an oscillating air pressure having a higher frequency than a respiration frequency of the patient, to the inhale gas flowing through the patient side path, an exhaust path that exhausts an exhale gas containing carbon dioxide exhaled from the patient, into the atmosphere, and an auxiliary inhale gas supply are also provided. The patient side path includes a branching pipe that branches a flow from the inhale gas introducer to the exhaust path side and the patient side and an intrachea insert tube that is connected to the patient side end of the branching pipe can be inserted through a mouth into the trachea of the patient.

15 Claims, 15 Drawing Sheets

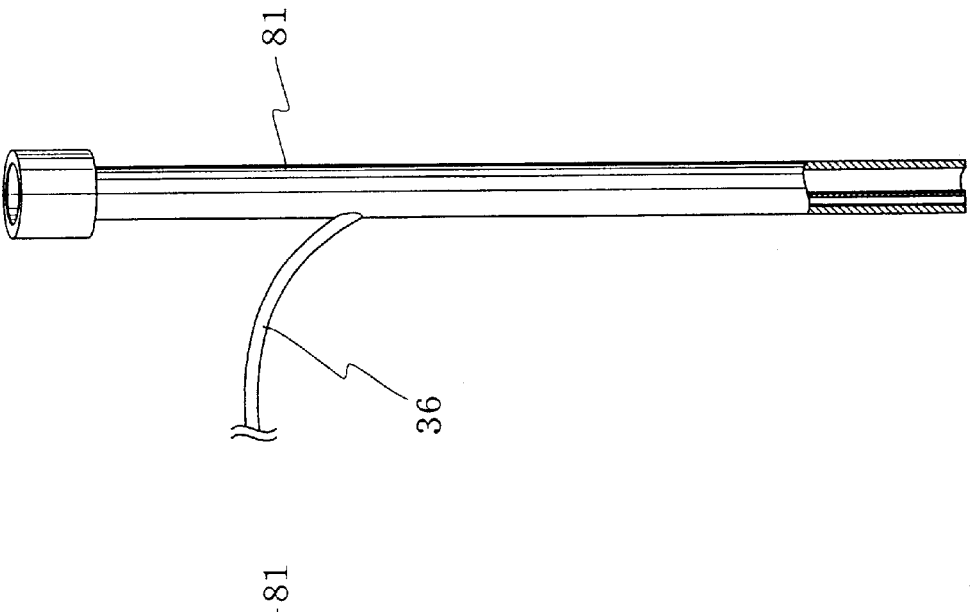
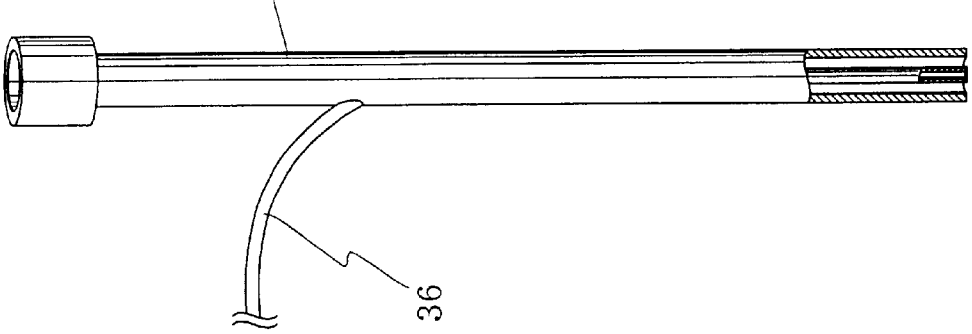
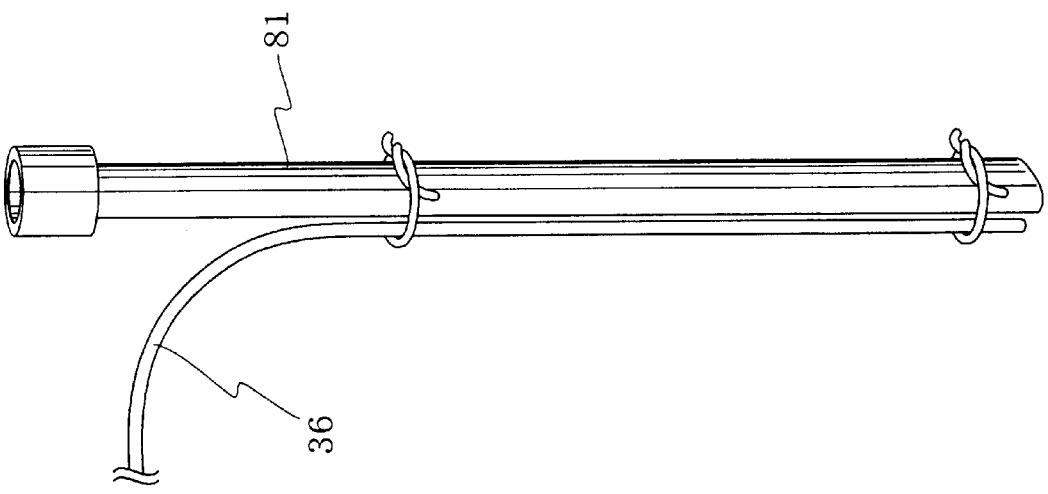

| Ventilation Condition | Partial Pressure of Carbon dioxide inn artery blood (PaCO$_2$) |
|---|---|
| HFO Condition 1 | 90 mmHg (1.2×10$^4$ [Pa]) |
| HFO Condition 2 | 44 mmHg (5.3×10$^3$ [Pa]) |
| HFO Condition 3 | 60 mmHg (8.0×10$^3$ [Pa]) |

| Inhale amount [ℓ/min] | 10 | 15 | 20 | 25 | 30 |
|---|---|---|---|---|---|
| $M_i$ | $M_1$ | $M_2$ | $M_3$ | $M_4$ | $M_5$ |

| Inner pressure $\begin{bmatrix} cmH_2O \\ (Pa) \end{bmatrix}$ | 5 (490) | 6 (588) | 7 (686) | 8 (784) | 9 (882) | 10 (980) | 11 (1078) | 12 (1176) | 13 (1274) | 14 (1372) | 15 (1470) |
|---|---|---|---|---|---|---|---|---|---|---|---|
| $M_{ij}$ | $M_{51}$ | $M_{52}$ | $M_{53}$ | $M_{54}$ | $M_{55}$ | $M_{56}$ | $M_{57}$ | $M_{58}$ | $M_{59}$ | $M_{5\alpha}$ | $M_{5\beta}$ |

| Frequency [Hz] | 3 | 6 | 9 | 12 | 15 |
|---|---|---|---|---|---|
| $M_{ijk}$ | $M_{561}$ | $M_{562}$ | $M_{563}$ | $M_{564}$ | $M_{565}$ |

$M_{56}$

HIGH-FREQUENCY OSCILLATION ARTIFICIAL RESPIRATION APPARATUS

BACKGROUND OF THE INVENTION

1. Field of the Invention

The present invention relates to an artificial respiration apparatus and in particular, to a high-frequency oscillation respiration apparatus.

2. Description of the Related Art

As shown in FIG. 16, in a conventional high-frequency oscillation aspiration apparatus 200, an inhale gas containing a high-concentration oxygen is supplied from an oxygen supply source 201 to flow through a fluid path system having a three-way branching pipe 202 for branching to a patient X and an exhale side. The inhale gas is urged by a high-frequency (3 to 15 Hz) oscillating air pressure generated by an oscillating air pressure urging unit 203 to flow with a flow rate of 10 to 30 [1/min] at a normal mode and 60 [1/min] at maximum for supplying oxygen to lungs of the patient X. Here, the average pressure applied to the lungs of the patient is controlled according to an open degree of a rubber valve of an inhale valve 204 provided at an outlet of the inhale gas. The average pressure is normally set so as to maintain 5 to 15 [cm $H_2O$] (490 to 1470 [Pa]) (hereinafter, the pressure values represent values added to the atmospheric pressure).

Explanation will be given on a principle of oxygen supply in the high-frequency oscillation artificial respiration apparatus 200. Firstly, when an inhale gas to be supplied to a patient is urged by a high-frequency oscillation oscillating air pressure, the pressure amplitude of the inhale gas causes a small-amount ventilation (gas exchange like convection) with respect to the gas containing carbon dioxide to be exhaled (hereinafter, referred to as an exhale gas). Simultaneously with this, vibration of the inhale gas causes a diffusion movement, which causes the inhale gas to intrude into the lungs via an in-trachea tube 207 and the exhale gas to be transferred out of the lungs (up to the mouth of the patient). A subsequent exhale gas portion performs the aforementioned ventilation and urges the exhale gas, which has been transferred out of the lungs, to be sent to the outlet. Thus, it is possible to maintain a constant oxygen concentration in the lungs of the patient.

Japanese Utility Model Publication (examined) 2-7569 discloses a high-frequency oscillation artificial respiration apparatus using a mechanical piston and electrical speaker vibration as an oscillating air pressure urging unit. However, these methods provide only a small amplitude of oscillating air pressure for urging the inhale gas and cannot perform a sufficient ventilation for lungs of a grow-up and have been used only for new-born babies.

In the high-frequency oscillation artificial respiration apparatus as shown in FIG. 16, which is disclosed in Japanese Patent Nos. 2798255, 2798256, and 2798257, a blower 205 and a rotary valve 206 are used as the oscillating air pressure urging unit 203 so as to improve the high-frequency oscillation oscillation.

Moreover, in the aforementioned high-frequency oscillation artificial respiration apparatus 200, the user (doctor) can set the following basic parameters according to the state of the patient: (1) inner pressure (5 to 15 [cm$H_2O$] (490 to 1470 [Pa]) of a flow path from the oxygen supply source to the patient x; (2) a ventilation amount per oscillation cycle with respect to the lungs of the patient (hereinafter, referred to as one ventilation amount against the lungs of the patient; more specifically, several to several hundreds of [ml] according to the weight of the patient; and (3) ventilation frequency (3 to 15 [Hz]) of the oscillating air pressure. In addition to these, there are accompanying parameters: an inhale gas supply amount and an inhale gas oxygen concentration of the inhale gas sent to the patient. According to the state of the patient, the aforementioned basic parameters are controlled as follows to control respiration.

(1) When oxidation is required, i.e., when it is necessary to increase the partial pressure of oxygen (Pa$O_2$) in the artery blood of the patient X, the average inner pressure in the flow path up to the patient is increased.

(2) When it is necessary to quickly exhaust carbon dioxide, i.e., when it is necessary to lower the partial pressure of carbon dioxide (Pa$O_2$) in the artery blood, one ventilation amount against the lungs of the patient is increased.

(3) The inherent frequency increasing the ventilation efficiency varies depending of each of the patients X as well as the state of the patient. The ventilation frequency is regulated so that the frequency is near the inherent frequency.

The ventilation frequency, at the initial stage, is determined according to the weight of the patient, and then adjusted to a frequency at which resonance is generated with the body of the patient X to increase the gas (oxygen) diffusion efficiency and the gas exchange (between oxygen and carbon dioxide) is effectively performed. In general, the ventilation frequency is set to about 15 {Hz} for a new-born baby and 3 to 10 {Hz} for a child or a grown-up.

During an artificial respiration, the ventilation frequency is normally fixed unless a sudden change is caused in the state of the patient X. The ventilation frequency is not often changed. Accordingly, normally, in order to perform a desired artificial respiration according to the state of the patient X, the respiration state is adjusted with the parameter (1) or (2).

In the aforementioned conventional high-frequency oscillation artificial respiration apparatus 200, the oscillating air pressure amplitude is increased by using a blower 205 having a large output, thus enabling to obtain a sufficient ventilation for lungs of a grown-up. FIG. 17 graphically shows an inner pressure change in the vicinity of the three-way branching pipe 202 during a high-frequency oscillation artificial respiration.

However, in the oscillating air pressure urging unit 203 of the aforementioned conventional high-frequency oscillation artificial respiration apparatus 200, the inner pressure amplitude (difference between the uppermost pressure and the lowermost pressure) in the vicinity of the three-way branching pipe 202 during a high-frequency oscillation artificial respiration exceeds 100 [cm $H_2O$] (9800 [Pa]) and accordingly, it is necessary to carefully adjust the pressure for a patient.

The pressure applied to lungs of a human being is a load to the lungs if the pressure is too high or too low. In the conventional example, the pressure amplitude is increased to perform a sufficient ventilation, which means that the pressure approaches the uppermost or the lowermost pressure. In order to perform a high-frequency oscillation artificial respiration without applying a load to the lungs of a patient, it is necessary to set the pressure with a great care.

Moreover, in the aforementioned high-frequency oscillation artificial respiration apparatus 200, even when the pressure is in a range not applying a load to a patient, a high-frequency oscillation artificial respiration with a large pressure amplitude causes a large vibration of the breast of the patient X, which is not preferable when a medical instrument of instillation or a catheter is applied to the patient X or when a measurement is to be performed using a measurement apparatus.

Furthermore, when the pressure amplitude is increased in the high-frequency oscillation artificial respiration apparatus 200, there arises a problem that the oscillating air pressure urging unit 203 causes a large noise and the power consumption is also increased.

Moreover, there is a case that the patient state is suddenly changed, resulting in an excessive decrease or increase of $PaO_2$. In such a case, the inherent frequency of the patient X has been changed and the adjustments of (1) and (2) alone are insufficient. The ventilation frequency should be changed.

However, when the ventilation frequency is changed, the oscillating flow state in the in-trachea tube is remarkably changed, which in turn changes the gas exchange effect by the patient, causing a further change in the patient. Especially at the ventilation frequency 3 to 10 {Hz} used for a child to a grown-up, a change of 1 [Hz] may remarkably change the gas convey mechanism and the doctor should be very careful when changing the ventilation frequency.

As has been described above, in the conventional high-frequency oscillation artificial respiration apparatus, the "one ventilation amount" and the "ventilation frequency" represent parameters affecting the partial pressure of carbon dioxide in the artery blood. That is, one cure index is affected by two factors and the high-frequency oscillation artificial respiration apparatus should be operated very carefully. For the doctor using the high-frequency oscillation artificial respiration apparatus, the "setting of the ventilation frequency" is a very complicated operation.

Doctors want a high-frequency oscillation artificial respiration apparatus capable of adjusting the ventilation frequency without causing a sudden change in the partial pressure of carbon dioxide in the artery blood of the patient.

SUMMARY OF THE INVENTION

It is therefore an object of the present invention to provide a high-frequency oscillation artificial respiration apparatus capable of performing a sufficient ventilation while reducing the pressure amplitude.

Moreover, an object of the present invention to provide a high-frequency oscillation (hereinafter, referred to as HFO) artificial respiration apparatus in which adjustment can be made without causing interactions between the aforementioned parameters.

The high-frequency oscillation artificial respiration apparatus disclosed in claim 1 comprises: an inhale gas introduction block for supplying an inhale gas containing oxygen to a patient, a patient side path for guiding the inhale gas from the inhale gas introduction block into the patient, an oscillating air pressure urging block for applying an oscillating air pressure having a higher frequency than a respiration frequency of the patient, to the inhale gas flowing through the patient side path, and an exhaust path for exhausting an exhale gas containing carbon oxide exhaled from the patient, into the atmosphere.

Furthermore, the patient side path includes a branching pipe for branching a flow from the inhale gas introduction block to the side of the exhaust path and the side of the patient and an in-trachea insert tube which is connected to the patient side end of the branching pipe and can be inserted through a mouth into lungs of the patient.

The apparatus further comprises an auxiliary inhale gas supply block for supplying an inhale gas up to the vicinity of the lungs of the patient through a path different from the patient side path. The auxiliary inhale gas supply block includes an inhale gas supply source and an auxiliary inhale gas supply path, which is different from the patient side path, for guiding the inhale gas from the supply source into the lungs of the patient.

In the aforementioned configuration, an inhale gas is generated from the inhale gas introduction block and set to a patient through the patient side path. Furthermore, the inhale gas flowing through the patient side path is urged by the oscillating air pressure urging unit. The inhale gas is divided by the branching pipe into the patient side path and the exhaust path. The inhale gas introduced into the patient side is driven by the positive pressure of the oscillating air pressure through the in-trachea insert tube to reach lungs of the patient, thus supplying oxygen to the lungs. On the other hand, an exhale gas containing carbon dioxide is driven by a negative pressure of the oscillating air pressure to flow through the in-trachea insert tube to the branching pipe and is pushed together with a subsequent inhale gas into the exhaust path to be exhausted into the atmosphere.

While the aforementioned ventilation is performed in the lungs, the auxiliary inhale gas supply block supplies an inhale gas from the inhale gas supply source through the auxiliary inhale gas supply path into the lungs of the patient. This auxiliary inhale gas supply path is separated from the patient side path and the gas is not urged by the oscillating air pressure. Moreover, the auxiliary inhale gas supply path is not connected to the exhaust path, either. Accordingly, the inhale gas is supplied slowly at a constant flow rate into the lungs. Accordingly, the exhale gas generated in the lungs is forced to be sent through the in-trachea insert tube into the exhaust path apart form the function of the negative pressure of the oscillating air pressure.

Moreover, the high-frequency oscillation (HFO) artificial respiration apparatus claimed in claim 12 comprises: an inhale gas introduction block for supplying an inhale gas containing oxygen to a patient; a patient side path for guiding the inhale gas from the inhale gas introduction block to the patient; an oscillating air pressure urging block for urging the inhale gas flowing in the patient side path with an oscillating air pressure having a cycle shorter than a respiration cycle of the patient; an exhaust path for exhausting into the atmosphere an exhale gas containing carbon dioxide exhaled from the patient; and a controller for controlling operation of the oscillating air pressure urging block.

The oscillating air pressure urging block can regulate a ventilation amount per oscillation cycle and an oscillating frequency of the oscillating air pressure. Moreover, the controller includes an entry block for accepting the oscillation frequency entered, and an operation control block for controlling the oscillating air pressure urging block to supply an output oscillating air pressure set to the oscillation frequency entered.

The operation control block has a ventilation state maintaining function for modifying the oscillation frequency according to an entered value in such a manner that a ventilation amount per oscillation cycle and an oscillation frequency of the oscillating air pressure are modified while maintaining a value of $V_T^2 \cdot f$ constant wherein $V_T$ represents a ventilation amount per oscillation cycle for lungs of the patient and f represents an oscillation frequency.

In the aforementioned configuration, an inhale gas is generated from the inhale gas introduction block and sent through the patient side path to the patient. Furthermore, the inhale gas flowing in the patient side path is urged by an oscillating air pressure from the oscillating air pressure urging block. The inhale gas is divided in a branching pipe to a patient side and an exhaust path side. The inhale gas flowing into the patient side is sent by the positive pressure of the oscillating air pressure through an in-trachea insert tube to reach the lungs of the patient, thus supplying oxygen to the lungs. Moreover, an exhale gas containing carbon dioxide generated from the lungs is caused by the negative pressure of the oscillating air pressure to flow through the in-trachea insert tube to the branching pipe and pushed together with a subsequent inhale gas into the exhaust path to be exhausted into the atmosphere.

When the ventilation efficiency of the patient is found to be low or the patient state has changed and the oscillation frequency should be set to a new value, the user (doctor) enters a new oscillation frequency value to the entry block through an external input unit connected to the entry block.

The operation control block stars an operation control to modify the oscillation frequency of the oscillating air pressure output from the oscillating air pressure urging block. That is, the oscillating air pressure urging block is regulated to be modified from the previous oscillation frequency to the oscillating frequency entered, upon this modification, the ventilation amount per oscillation cycle is also modified according to the modification of the oscillation frequency. That is, control is performed to modify the oscillation frequency f and the ventilation amount per oscillation cycle so that the one ventilation amount $V_T$ for the lungs of the patient and the oscillation frequency f satisfy the condition $V_T^2 \cdot f = \text{constant}$.

It should be noted that the aforementioned "ventilation amount per oscillation cycle" represents an oscillation amount per one oscillation cycle of the oscillating air pressure directly output from the oscillating air pressure urging block, and the "one ventilation amount for lungs of the patient" represents a ventilation amount actually ventilated per oscillation cycle by the oscillating air pressure which has reached the lungs of the patient.

The "ventilation amount per oscillation cycle" and the "one ventilation amount for lungs of the patient" may not coincide with each other but they change with a steady interrelationship between them. Accordingly, when the target "one ventilation amount for lungs of the patient" is known in advance, a corresponding "ventilation amount per oscillation cycle" can be identified. The operation control of the oscillating air pressure urging block is performed so as to obtain the target "ventilation amount per oscillation cycle".

The present invention achieves the aforementioned object by the aforementioned configuration.

BRIEF DESCRIPTION OF THE DRAWINGS

FIG. 3 explains an in-trachea insert tube and an auxiliary supply insert tube shown in FIG. 1. FIG. 3(A) shows an example of the tubes, FIG. 3 (B) shows another example of the tubes, and FIG. 3 (C) shows still another example of the tubes.

FIG. 6 shows test results.

FIG. 9 explains a concept of a first stage map of a 5-dimensional map.

FIG. 10 explains a concept of a second stage map of the 5-dimensional map.

FIG. 11 explains a concept of a third stage map of the 5-dimensional map.

DESCRIPTION OF THE PREFERRED EMBODIMENTS

<Embodiment 1>

(Entire Configuration)

Figure 1:
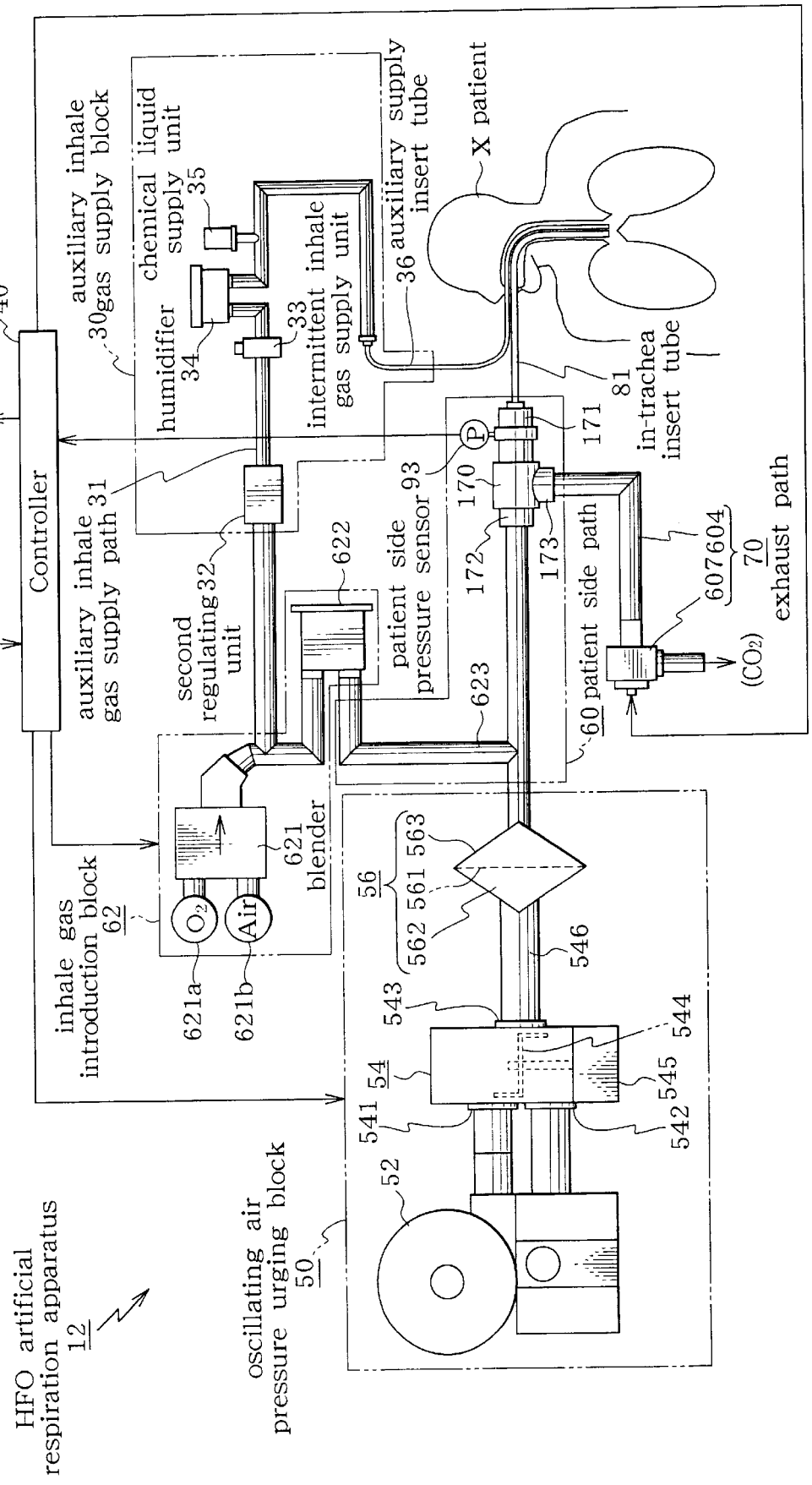
FIG. 1 is a block diagram showing a configuration of a high-frequency oscillation artificial respiration apparatus according to a first embodiment.

Explanation will be given on the first embodiment of the present invention with reference to FIG. 1 to FIG. 4. FIG. 1 is a block diagram showing a configuration of a high-frequency oscillation artificial respiration apparatus 12 according to the present embodiment.

The high-frequency oscillation artificial respiration apparatus 12 includes: an inhale gas introduction block 62 for supplying an inhale gas containing oxygen to a patient X; a patient side path 60 for guiding the inhale gas from the inhale gas introduction block 62 to the patient X; an oscillating air pressure urging block 50 for urging an oscillating air pressure having a cycle higher than the respiration cycle of the patient X; an exhaust path 70 for exhausting to the atmosphere an exhale gas containing carbon dioxide from the patient X; an auxiliary inhale gas supply block 30 for supplying an inhale gas into lungs of the patient X through a path different from the patient side path 60; and a controller for controlling operations of the aforementioned blocks.

Hereinafter, explanation will be given on each of the blocks.

(Inhale gas introduction block)

The inhale gas introduction block 62 is connected to an oxygen supply port 621a and an air supply port 621b, and includes: a blender 621 serving as a first adjustment unit for mixing the oxygen and the air, and a humidifier for humidifying the air sent out of the blender 621.

The oxygen supply port 621a is a cylinder containing oxygen or a supply-valve provided in a hospital. Similarly, the air supply port 621b is a cylinder containing air or a supply valve provided in a hospital. These supply ports 621a and 621b supply oxygen and air with a constant pressure to the blender.

The blender 621 has a flow rate regulating valve (not depicted) at a connection portion with the supply port 621a and at a connection portion with the supply port 621b. By adjusting these regulating valves, it is possible to adjust the oxygen concentration of the inhale gas. Moreover, the blender 621 has a plurality of output valves (not depicted) for flowing the inhale gas to the side of the humidifier 622. Each of the output valves has a different flow rate. By selecting an output valve of a desired flow rate, it is possible to supply the inhale gas at a predetermined flow rate. It should be noted that the oxygen concentration and the flow rate of the inhale gas are automatically set by an operation signal from the controller 40.

The humidifier 622 is connected to an inhale gas pipe 623 for supplying the inhale gas humidified to the patient X. The inhale gas pipe 623 is branched to two directions: one leads to a pressurized chamber 563 of a diaphragm mechanism 56 which will be detailed later and the-other leads to a three-way branching pipe 170 which will be detailed later.

(Oscillating air pressure urging block)

The oscillating air pressure urging block 50 includes: a blower 52 for simultaneously generating a positive air pressure and a negative air pressure; a rotary valve mechanism 54 for alternately selecting the positive pressure and the negative pressure generated in the blower 52 and converting them into a predetermined oscillating air pressure; and a diaphragm mechanism 56 operated by the oscillating air pressure from the rotary valve mechanism 54, so as to urge an oscillating air pressure to the inhale gas supplied from the inhale gas introduction block 62 to the patient X.

Figure 16:
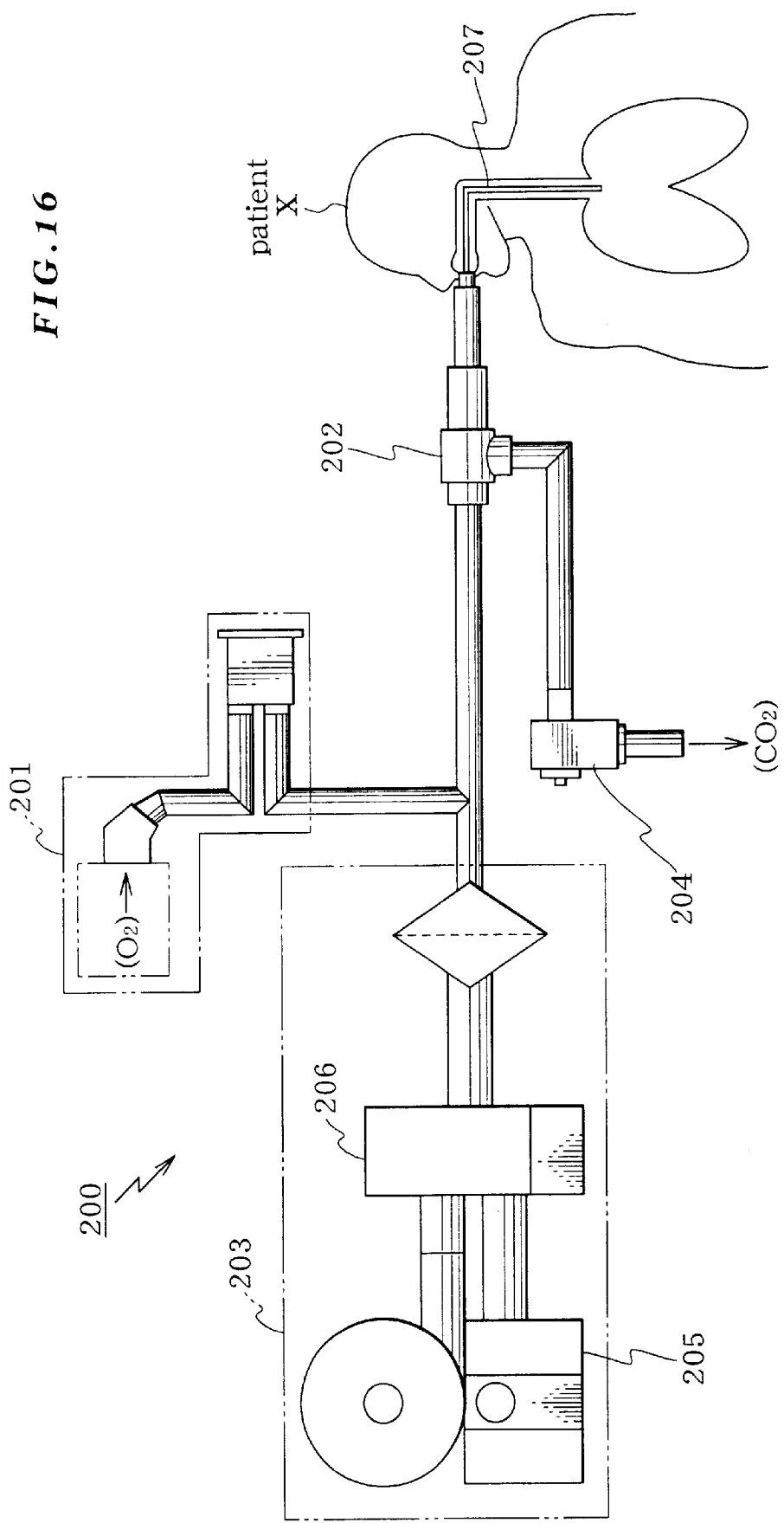
FIG. 16 is a block diagram showing a conventional apparatus.
Figure 17:
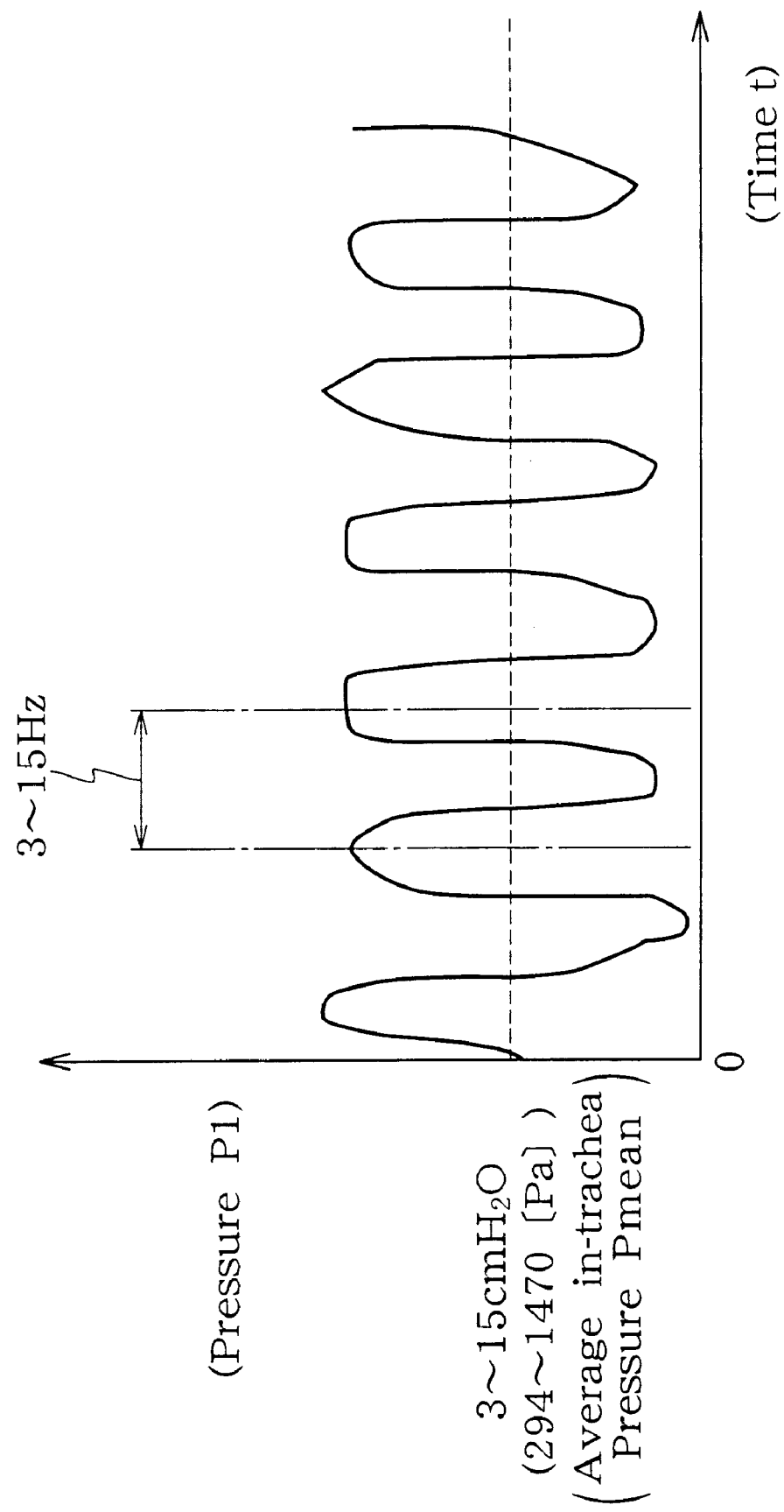
FIG. 17 shows a change in an inner pressure in the vicinity of the three-way branching pipe during a conventional high-frequency oscillation artificial respiration.

The blower 52 takes in the air and sends out the air so as to simultaneously generate a positive pressure and a negative pressure. The blower 52 has a smaller output than that of the blower 205 (FIG. 16) in the conventional example. Accordingly, a ventilation amount by the oscillating air pressure is smaller than in the conventional example (for example 15 [ml]). The blower 52 has an air inlet opening connected to a negative pressure port 542 of the rotary valve mechanism 54 which will be detailed later and an air outlet opening connected to a positive pressure port 541.

The rotary valve mechanism 54 includes: a positive pressure port 541 fed with a positive pressure from the blower 52; a negative pressure port 542 urged with a negative pressure from the blower 52; an output port 543 for outputting an oscillating air pressure; a rotary valve 544 for alternately connecting the output port 543 to the positive pressure port 541 and to the negative pressure port 542; and a drive block 545 for rotating the rotary valve 544.

The drive block includes a motor and a reducer (not depicted) for rotating the rotary valve 544 at 900 [rpm]. While the rotary valve 544 makes one turn, the port 541 is connected to the port 543 and then the port 542 is connected to the port 543. Thus, an oscillating air pressure Apn having a frequency of 15 [Hz] is applied to the inhale gas supplied. The port 543 is connected to an oscillating air pressure pipe 546 for transmitting the oscillating air pressure Apn to the diaphragm mechanism 56.

The diaphragm mechanism 56 includes: a pressurizing chamber 562; a pressurized chamber 563; and a diaphragm 561 made from a expandable film member serving as a partition between the pressurizing chamber 562 and the pressurized chamber 563. The pressurizing chamber 562 is connected via the oscillating air pressure pipe 564 to the output port 543 of the rotary valve 54 while the pressurized chamber 563 is connected to the inhale pipe 623. With this configuration, the oscillating air pressure obtained by the rotary valve is applied via the diaphragm 561 to the inhale gas flowing in the inhale pipe 623.

(Patient side path)

Furthermore, the high-frequency oscillation artificial respiration apparatus 12 includes a three-way branching pipe 170 at the downstream of the inhale pipe 623. The three-way branching pipe 170 branches the downstream side to the patient X and to an exhaust path. The three-way branching pipe 170 has three pipe paths: a patient side pipe path 171 (patient side end), an oxygen supply port side pipe path 172, and an exhale gas exhaust side pipe path 173. These pipe paths are interconnected inside. The oxygen supply port side pipe path 172 is connected to the inhale gas pipe 623 while the patient side pipe path 171 is connected to the in-trachea insert tube 81. The three-way branching pipe 170, the inhale gas pipe 623, and the in-trachea insert tube 81 constitute the patient side path 60. Moreover, the patient side pipe path 171 has a patient side pressure sensor 93 for detecting an average in-path pressure. The pressure detected is fed to the controller 40.

The in-trachea insert tube 81 is inserted from the mouth to the trachea of the patient up to the branching point (first branching) to the right and the left bronchus. Accordingly, the in-trachea insert tube 81 has a length from the mouth to the first branching point and an outer diameter that can be inserted into the trachea.

It should be noted that the in-trachea insert tube 81 has length and outer diameter set for average grownups and not for a particular patient X. For example, a grown-up male has an average length of 22 to 26 [cm] from the mouth to the first branching point. The three-way branching pipe 170 has the patient side pipe path 171 whose end is located at about 3 to 5 cm from the mouth of the patient. Accordingly, the in-trachea insert tube 81 need to have a total length of about 25 to 31 [cm]. In this embodiment, the length is set to 30 [cm]. Moreover, when consideration is taken for grown-ups, the in-trachea insert tube 81 has an inner diameter of about 8 [mm].

Furthermore, the in-trachea insert tube 81 is detachably attached to the patient side pipe path 171 of the three-way branching pipe 170. Accordingly, after used for an artificial respiration, the in-trachea insert tube 81 is disconnected and discarded or sterilized for re-use.

(Exhaust path)

Furthermore, the exhale gas exhaust pipe path 173 of the three-way branching pipe 170 is connected to one end of the exhaust pipe 604, the other end of which is connected to a flow rate regulating valve 607. The exhaust pipe 604 and the flow rate regulating valve 607 constitutes the exhaust path 70 for the exhale gas containing carbon dioxide exhausted from the lungs of the patient to be exhausted into the atmosphere.

Figure 2:
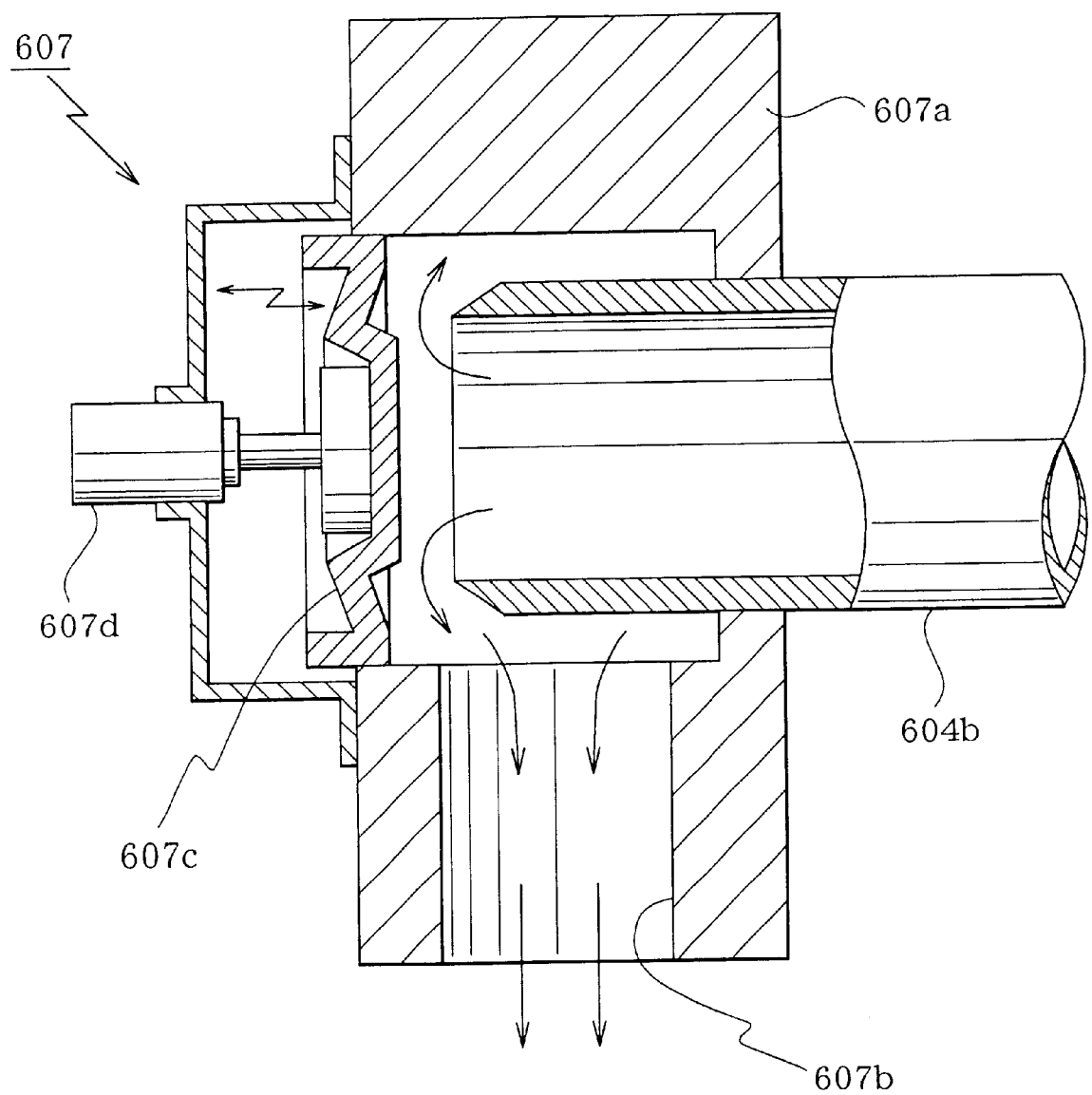
FIG. 2 is a cross sectional view of a flow rate regulating valve shown in FIG. 1.

FIG. 2 is an enlarged view of the exhaust path 70 partially cut off. As shown in this figure, the flow rate regulating valve 607 includes a frame 607a, an exhaust port 697b, a flow rate regulating movable valve (control silicon sheet) 607c, and a solenoid 607d as a reciprocal urging mechanism for advancing and retrieving the movable valve 607c in a constant direction.

This solenoid 607d moves the movable valve by an amount according to the control signal from the controller 40. Thus, the exhale gas exhaust amount of the flow rate regulating valve 607 is automatically regulated.

(Auxiliary supply block)

The auxiliary inhale gas supply block 30 includes a supply source and an auxiliary inhale gas supply path 31 for guiding an inhale gas from the supply port to the lungs of the patient X through a path which is different from the patient side path 60. The auxiliary inhale gas supply block 30 utilizes the aforementioned exhale gas introduction block 62 as the inhale gas supply source. That is, the upstream end of the auxiliary inhale gas supply path 31 is connected to a pipe connecting the blender 621 and the humidifier 622 of the exhale gas introduction block 62. The inhale gas sent from the blender 621 flows through the patient side pipe path 60 and the auxiliary inhale gas supply path 30. Accordingly, the inhale gas flowing through the auxiliary inhale gas supply path 31 and the inhale gas flowing through the patient side pipe path 60 have an identical oxygen concentration.

In the middle of the aforementioned auxiliary inhale gas supply path 31, there is provided a second regulating unit 32 for regulating the flow rate of the inhale gas flowing through the auxiliary inhale gas supply path 31. This second regulating unit 32 is connected to the controller 40. According to the operation signal from the controller, the flow rate of the inhale gas flowing through the auxiliary inhale gas supply path 31 is increased or decreased.

Furthermore, at the downstream of the second regulating unit, there is provided an intermittent inhale gas supply unit 33 for regulating at a repeated constant cycle the inhale gas flow in the auxiliary inhale gas supply path 31. This intermittent inhale gas supply unit 33 is, for example, a rotary valve which is rotated by a drive motor owned by itself, so as to repeat a passage and stop of the inhale gas at a constant cycle. The inhale gas flowing in the auxiliary gas supply path 31 flows with a constant pressure toward the patient side by the supply pressure from the oxygen supply port 621*a* and the air supply port 621*b*. Accordingly, the repetition of the open and closed state of the intermittent inhale gas supply unit 33 performs an inhale gas supply repeating a flow and stop. This intermittent inhale gas supply unit 33 is connected to the controller 40 and repeats the open and close operation according to the operation signal from the controller 40.

Furthermore, at the downstream of the intermittent inhale gas supply unit 33, the humidifier 34 is provided as an auxiliary humidifying unit for humidifying the inhale gas in the auxiliary inhale gas supply path 31. At a further downstream, there is provided a nebulizer 35 is provided as a chemical liquid supply unit for supplying chemical liquid into the auxiliary inhale gas supply path 31. This nebulizer has a so-called venturi structure and normally, the communication with the auxiliary inhale gas supply path 31 is closed. For example, when administration of a chemical for curing or a disinfectant chemical to the lungs of the patient X is required, the chemical liquid is administered from here. The chemical liquid is sent together with the inhale gas to the lungs of the patient X.

The auxiliary inhale gas supply path 31 has an auxiliary supply insert tube 36 which can be inserted into the trachea of the patient X. The auxiliary supply insert tube 36 has a length sufficient to reach the first branching point from the mouth of the patient X and an outer diameter which can be inserted into the trachea (together with the in-trachea insert tube 81).

Furthermore, this auxiliary supply insert tube 36 is detachably attached to the auxiliary inhale gas supply path 31 and can easily be replaced. After used for an artificial respiration, it can be removed and discarded or sterilized for re-use.

The auxiliary supply insert tube 36 and the in-trachea insert tube 81 are simultaneously inserted into the trachea of the patient X. Accordingly, as shown in FIG. 3 (A), they are attached to each other from the insert end to the intermediate portion. Moreover, as shown in FIGS. 3 (B) and (C), the auxiliary supply insert tube 36 and the in-trachea insert tube 81 may be formed as a unitary block. That is, the auxiliary supply insert tube 36 is inserted into the in-trachea insert tube 81 in the vicinity of the three-way branching pipe 170, thus forming a double tube. In FIG. 3 (B), the double tube has a cross sectional view showing coaxial circles of the auxiliary supply insert tube 36 surrounded by the intrachea insert tube 81. In FIG. 3 (C), the auxiliary inhale gas insert tube 36 is formed in contact with the inner wall of the in-trachea insert tube 81.

When such a double tube is used, the inhale gas flowing in the in-trachea insert tube 81 and the inhale gas flowing in the auxiliary supply insert tube 36 reache the end portion of the tube without being mixed. Moreover, when the configuration of FIG. 3 (B) or FIG. 3 (C) is used, it is possible to smoothly insert the tube into the trachea of the patient X.

(Controller)

Figure 4:
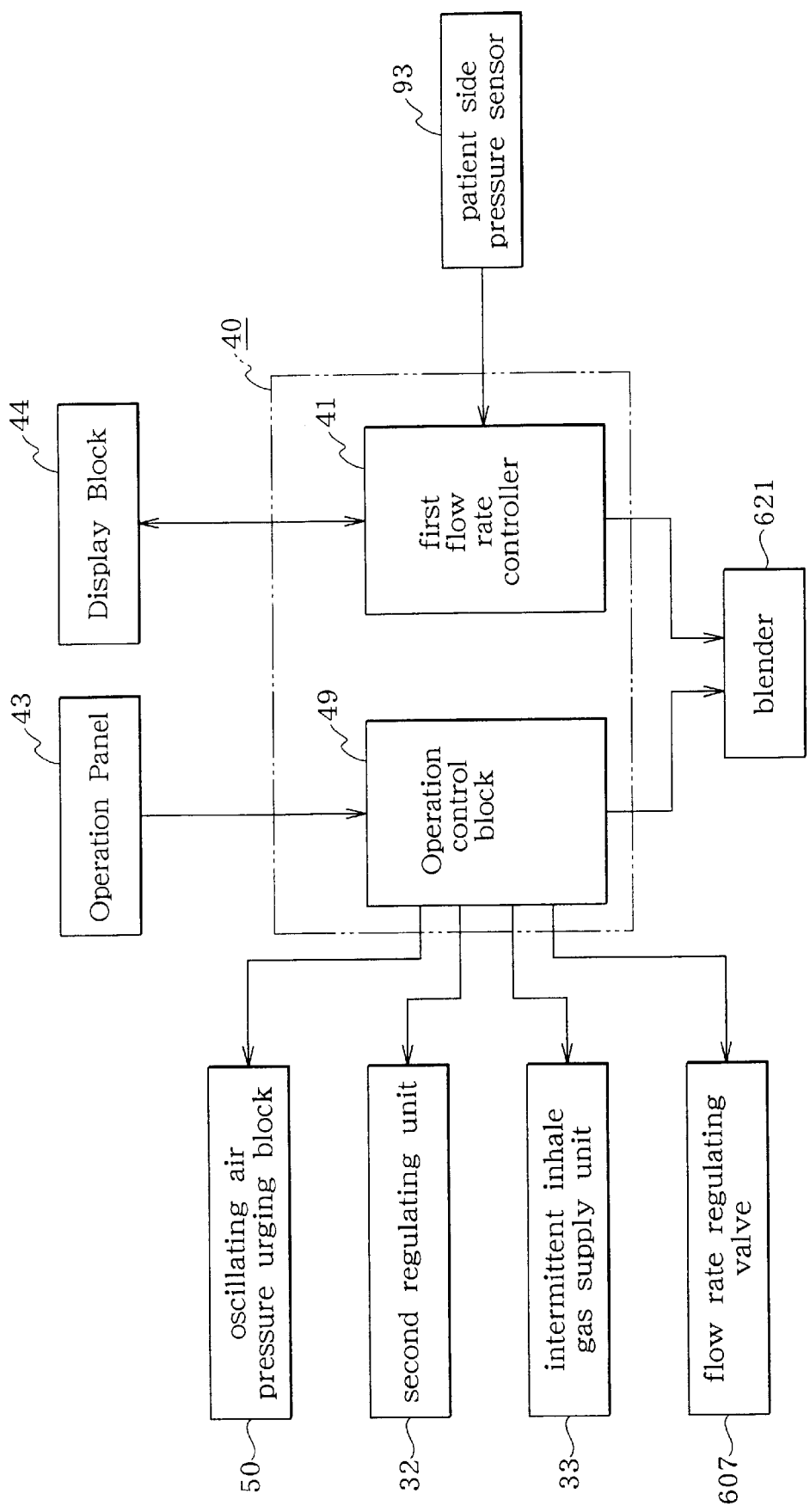
FIG. 4 is a block diagram showing a control system of the high-frequency oscillation artificial respiration apparatus.

Next, explanation will be given on the controller 40 with reference to FIG. 1 and FIG. 4. FIG. 4 is a block diagram showing a control system of the high-frequency oscillation artificial respiration apparatus 12. The controller 40 includes a CPU, a ROM, an A/D converter, and a program for executing an operation control of the high-frequency oscillation artificial respiration apparatus.

The controller 40 also includes an operation panel 43 for entering operation conditions of the respective components and a display unit 44 for displaying a detected pressure of the patient side pressure sensor 93.

Furthermore, the controller 40 includes an operation control block 49 for controlling the blender 621, the oscillating air pressure urging unit 50, the second regulating unit 32, the intermittent inhale gas supply unit 33, and the flow rate regulating valve 607; and a first flow rate controller 41 for controlling the blender 621 according to the detected pressure of the patient side pressure sensor 93.

(Operation of Embodiment 1)

Explanation will be given on the operation of the high-frequency oscillation artificial respiration apparatus including the control by the controller 40.

Firstly, the in-trachea insert tube 81 and the auxiliary supply insert tube 36 are inserted into the trachea of the patient X. Then, the operation panel 43 is operated to enter the vibration frequency of the oscillating air pressure urging unit 50, the oxygen concentration of the inhale gas, supply flow rate of the inhale gas (the total flow of the inhale gas flowing in the patient side path 60 and the auxiliary inhale gas supply path 31 such as 10 to 60 [1/min] at maximum, the inhale gas flow rate in the auxiliary inhale gas supply path 31, the intermittent flow frequency of the inhale gas in the auxiliary inhale gas supply path 31, and the upper limit and the lower limit of the patient supply pressure.

The operation controller 49 controls the blender 621 so as to mix oxygen and air according to the concentration value entered and selects to open a valve having the flow rate entered. Thus, an inhale gas of the selected concentration is supplied at the selected flow rate to the downstream of the blender. The inhale gas flows via the humidifier 622 to the inhale pipe 623 and the auxiliary inhale gas supply path 31.

The inhale gas flowing into the inhale gas pipe 623 is added by the oscillating air pressure from the oscillating air pressure urging unit 50. Here, the cycle of the oscillating air pressure is regulated to be the cycle entered by the operation controller 49 through the rotary valve 54.

The inhale gas flows via the three-way branching pipe 170 to the patient side path 171 and the exhale gas exhaust pipe path 173. The inhale gas flowing into the patient side pipe path 171 is introduced via the intrachea insert tube 81 into the lungs of the patient X by the positive pressure of the oscillating air pressure, thus supplying oxygen to the lungs. Moreover, the inhale gas which has contained carbon dioxide and has turned into an exhale gas is introduced by the negative pressure of the oscillating air pressure into the in-trachea insert tube 81 to reach the three-way branching pipe 170 and is pushed together with a subsequent inhale gas to the exhaust path 70 to be exhausted into the atmosphere. Here, the blower 52 used has a small outlet opening and accordingly, the pressure amplitude of the oscillating air pressure is reduced. Accordingly, even if an inhale gas is actively supplied from the auxiliary inhale gas supply path into the lungs, the exhale gas can smoothly be exhausted from the in-trachea insert tube 81.

On the other hand, at the side of the auxiliary inhale air supply path 31, the operation controller 49 controls the second regulating unit 32, so that the flow rate inside the auxiliary inhale gas supply path 31 is set to the specified flow rate with respect to the total inhale gas flow rate. Simultaneously with this, the intermittent inhale gas supply unit 33 is controlled in open/close speed so as to be at a cycle specified.

Thus, the inhale gas flowing in the auxiliary inhale gas supply path 31 is humidified while passing through the humidifier 34 and supplied via the auxiliary supply insert tube 36 into the lungs of the patient X. This auxiliary inhale gas supply path 31 is separated from the patient side path 60 and not urged by the oscillating air pressure. The auxiliary inhale supply path 31 is not connected to the exhaust path 70, either. Accordingly, the auxiliary inhale gas supply path 31 supplies the inhale gas into the lungs slowly and constantly. This forces the exhale gas generated in the lungs, to be sent via the in-trachea insert tube 81 into the exhaust path 70, apart from the function of the negative pressure of the oscillating air pressure.

Moreover, the patient side pressure sensor 93 detects the inner pressure in the three-way branching pipe 170 fluctuating together with the fluctuation of the pressure in the lungs due to the inhale gas supply and the detected result is output to the first flow rate controller 41. The first flow rate controller 41 displays the detected pressure on the display block 44. The user (for example, doctor) of the high-frequency oscillation artificial respiration apparatus 12 references the detected pressure displayed on the display block 44 and operates the operation panel 43 to enter the open degree of the flow regulating valve 607 so as to adjust the exhale gas exhaust flow rate via the operation controller 49 so that the lungs of the patient are under a preferable pressure.

Moreover, even when no operation is performed by a doctor, the first flow rate controller 41 performs the following control. That is, when the detected pressure exceeds the upper limit of the patient supply pressure specified in advance, the inhale gas supply flow rate from the blender 621 is automatically reduced. The upper limit is, for example, the atmospheric pressure added by 5 to 15 [cm $H_2O$] (490 to 1470 [Pa]) and by 40 [cm $H_2O$] (3920 [Pa]). On the other hand, when the detected pressure is lower than the lower limit of the patient supply pressure specified in advance, control is performed so as to increase the inhale gas supply flow rate from the blender 621. Here, the lower limit is, for example, an atmospheric pressure added by 5 to 15 [cm $H_2O$] (490 to 1470 {Pa]) and deleted by 40 [cm $H_2O$] (3920 [Pa]).

As has been described above, in the present embodiment, there is provided the auxiliary inhale gas supply block 30 for supplying the inhale gas into the lungs of the patient apart from the patient side path 60 and accordingly, the inhale gas is actively supplied into the lungs of the patient separately from the ventilation by the high-frequency oscillation oscillation. This enables to perform a sufficient ventilation in the lungs and maintain a sufficient oxygen concentration without increasing the amplitude of the oscillating air pressure. Thus, it is possible to evade generation of the load due to high pressure or low pressure upon the lungs on the patient X and to maintain a preferable artificial respiration.

Moreover, since the oscillating air pressure amplitude can be reduced, it is possible to suppress the vibration of the lungs of the patient, so as not to affect the other medical instruments for curing or measurement.

Furthermore, since the pressure amplitude can be reduced, it becomes possible to reduce the output of the oscillating air pressure urging unit 50 or to replace it with one having a lower output. This reduces the noise and power consumption as well as to reduce the apparatus size and weight.

Furthermore, in the present embodiment, the auxiliary inhale gas supply block 30 uses the inhale gas introduction block 62 as the inhale gas supply source and accordingly, there is no need of an independent inhale gas supply source, thus increasing the apparatus productivity and reducing the apparatus size and weight.

Moreover, the auxiliary supply insert tube 36 is provided at the end of the patient side of the auxiliary inhale gas supply path 31. Accordingly, it is possible to directly send the inhale gas into the depth of the lungs of the patient X, thus improving the ventilation efficiency.

Furthermore, since the auxiliary supply insert tube 36 is formed with the in-trachea insert tube 81 as a unitary block without mixing the gasses between them, it is possible to smoothly insert the tubes into the trachea of the patient X and the inhale gas supplied from the auxiliary supply insert tube 36 is directly sent into the lungs, enabling to perform ventilation in the lungs effectively before being exhausted through the in-trachea insert tube 81.

Moreover, in the present embodiment, the intermittent inhale gas supply unit 33 is provided for regulating the inhale gas flow in the auxiliary inhale gas supply path 31 at a constant cycle. Accordingly, the inhale gas supply from the auxiliary inhale gas supply path 31 is an intermittent discharge which enhances the oxygen diffusion effect within the lungs and the ventilation efficiency.

Furthermore, in the present embodiment, the humidifier 34 is provided in the auxiliary inhale gas supply path 31. Accordingly, it is possible to humidify the inhale gas supplied from the auxiliary inhale gas supply path 31. This prevents drying of the inside of the lungs, enabling to perform the artificial respiration in a preferable state.

Furthermore, in the present embodiment, the chemical liquid supply unit 35 is provided in the auxiliary inhale gas supply path 31. Accordingly, it is possible to supply a chemical liquid into the lungs as is required while maintaining the high-frequency oscillation artificial respiration. Thus, it is possible to perform an effective curing of the patient.

Moreover, in the present embodiment, the controller 40 includes the first flow rate controller 41 for controlling the inhale gas flow rate of the blender 621. This enables to prevent an excessive rise or drop of the inhale gas pressure and to perform the artificial respiration without applying a load to the lungs of the patient. Moreover, it is possible to regulate the inhale gas flow rate and the inhale gas pressure without operation by the user.

<Embodiment 2>

Figure 5:
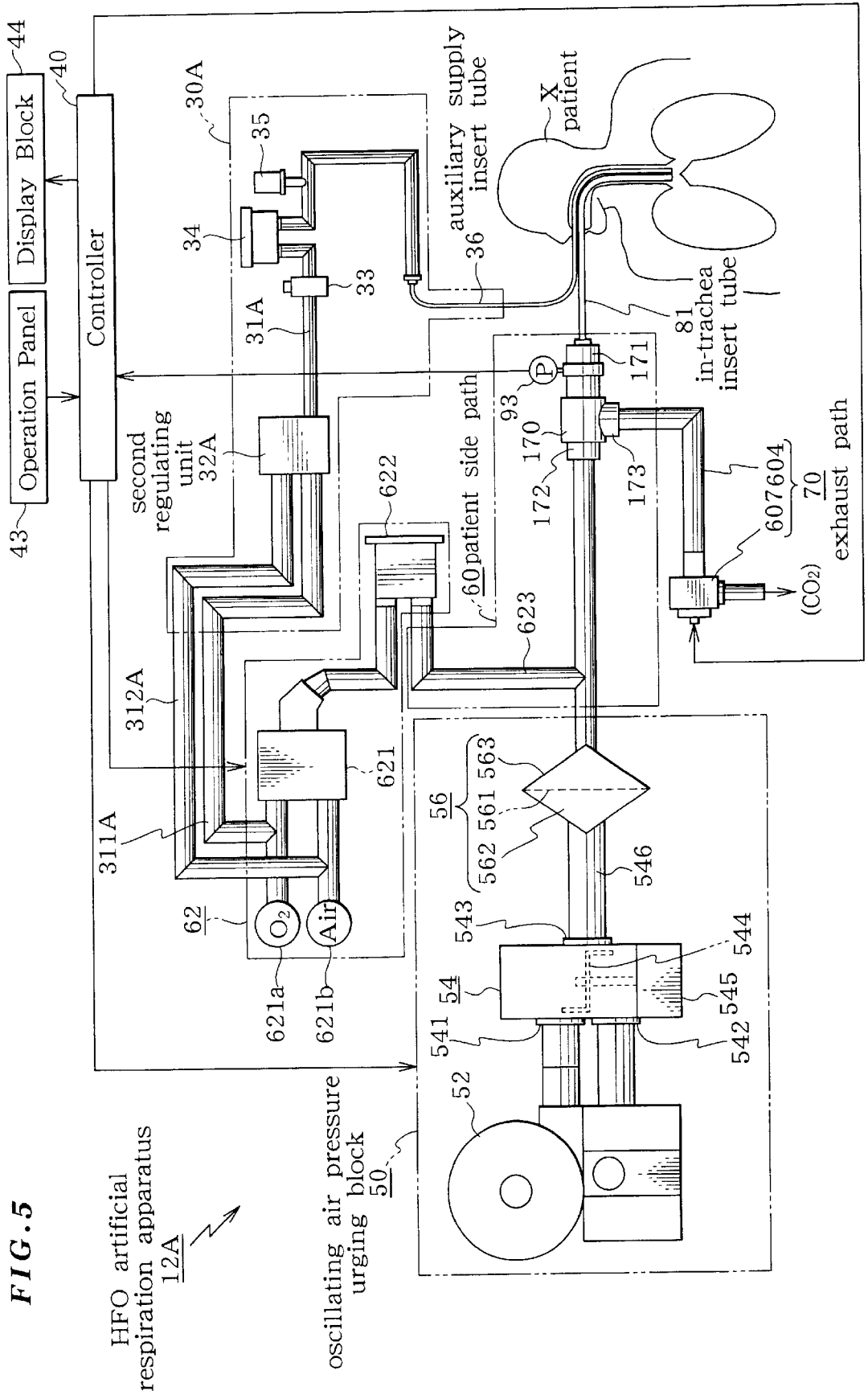
FIG. 5 is a block diagram showing a high-frequency oscillation artificial respiration apparatus according to the second embodiment.

Explanation will be given on a second embodiment of the present invention with reference to FIG. 5. FIG. 5 is a block diagram showing a configuration of a high-frequency oscillation artificial respiration apparatus 12A according to the present embodiment. This high-frequency oscillation artificial respiration apparatus 12A is identical to the aforementioned high-frequency oscillation artificial respiration apparatus 12 except for that the oxygen and the air from the oxygen supply port 621a and the air supply port 621b are directly fed to the auxiliary inhale gas supply block 30A without passing through the blender 621 of the inhale gas introduction block 62. Accordingly, in this embodiment, explanation will be given only on the auxiliary inhale gas supply block 30A, omitting the explanation of the other components denoted with like symbols.

The auxiliary inhale gas supply path 31A of the auxiliary inhale gas supply block 30A has an oxygen introduction pipe 311A and an air introduction piped 312A which are directly connected to the oxygen supply port 621a and the air supply port 621b, respectively. The introduction pipes 311A and 312A connects the supply ports 621a and 621b to the second regulating unit 32A.

This second regulating unit 32A, unlike the aforementioned second regulating unit 32, can regulate not only the inhale gas supply flow rate but also the oxygen concentration. That is, the second regulating unit 32A has valves (not depicted) capable of regulating flow rates arranged at the connection portions to the supply ports 621a and 621b and by regulating these valves, it is possible to regulate the oxygen concentration of the inhale gas. Moreover, the second regulating unit 32A has a plurality of output valves (not depicted) for flowing the inhale gas toward the downstream. The plurality of valves have different flow rates and by selecting an output valve of a desired flow rate, it is possible to supply a predetermined amount of inhale gas. It should be noted that the oxygen concentration and the flow rate of the inhale gas are automatically performed according to an operation signal from the controller 40.

The auxiliary inhale gas supply block 30A having the aforementioned configuration enables to set the flow rate and the oxygen concentration of the inhale gas to be flown to the auxiliary inhale gas supply path 31A without being affected by the flow rate and the oxygen concentration of the inhale gas set at the blender 621. It should be noted that the flow rate and the oxygen concentration of the inhale gas are specified through the operation panel 43 like in the case of the blender 621, and the second regulating unit 32A is controlled according to the entered values through the operation controller d49 of the controller 40.

Thus, the high-frequency oscillation artificial respiration apparatus 12A not only has the effects of the high-frequency oscillation artificial respiration apparatus 12 but also enables to obtain various combinations between the flow rate and the oxygen concentration of the inhale gas supplied form the patient side path and the flow rate and the oxygen concentration of the inhale gas supplied from the auxiliary inhale gas supply path 31A. Thus, it is possible to perform a high-frequency oscillation artificial respiration according to various states of the patient.

It should be noted that the high-frequency oscillation artificial respiration apparatus 12 has the first flow rate controller 41 for controlling the inhale gas supply amount of the blender 621 according to the output from the patient side pressure sensor 93. In the high-frequency oscillation artificial respiration apparatus 12A, the controller 40 may include a second flow rate controller for controlling the inhale gas supply amount of the second regulating unit 32A according to an output from the patient side pressure sensor 93. In this case also, the supply amount is controlled to be increased or decreased, so that a detected pressure does not exceed the upper limit or the lower limit. Thus, it is possible to obtain the same effect as the first flow rate controller 41.

Alternatively, the controller 40 may include a valve controller for regulating a valve open degree of the flow rate regulating valve 607 according to an output from the patient side pressure sensor 93. That is, when the detected pressure exceeds the upper limit, the flow rate regulating valve 607 is set to a larger open degree and when the detected pressure is lower than the lower limit, the flow rate regulating valve 607 is set to a smaller open degree. Thus, it is possible to obtain the same effect as the first flow rate controller 41.

Moreover, in the high-frequency oscillation artificial respiration apparatuses 12 and 12A, the auxiliary inhale gas supply block 30 and 30A may have an independent oxygen supply port and an air supply port without using the oxygen supply port 621a and the air supply port 621b of the inhale gas introduction block 62.

Moreover, in the aforementioned high-frequency oscillation artificial respiration apparatuses 12 and 12A, the patient side pressure sensor 93 is arranged at the patient side pipe path 171 of the three-way branching pipe 170. However, the position of the patient side pressure sensor 93 is not limited to this position and may be at any position in the vicinity of the patient. For example, the patient side pressure sensor may be arranged at the auxiliary supply insert tube 36.

[EXAMPLES]

Using the aforementioned high-frequency oscillation artificial respiration apparatus 12 and a conventional high-frequency oscillation artificial respiration apparatus not having the auxiliary inhale gas supply port 30, an artificial respiration was performed on an animal: a female hog (weight 17 [kg]m corresponding to a human of 5 or 6 years old).

Test Condition (1)

(Using a conventional high-frequency oscillation artificial respiration apparatus)

Ventilation frequency: 15 Hz

Average in-trachea pressure (intermediate amplitude pressure): 15 [cm $H_2O$] (1470 [Pa])

Ventilation amount: 20 [ml] at once

Inhale gas supply amount: 20 [1/min]

Inhale gas oxygen concentration: 100 [%]

In-trachea insert tube: Inner diameter 5 [mm]

Test Condition (2)

(Using the high-frequency oscillation artificial respiration apparatus 12)

Ventilation frequency: 15 Hz

Average in-trachea pressure: 15 [cm $H_2O$] (1470 [Pa])

Ventilation amount: 20 [ml] at once

Inhale gas supply amount (total of the patient side path and the auxiliary inhale gas supply path): 24 [1/min]

Inhale gas supply amount (flow rate of the auxiliary inhale gas supply path): 4 [1/min]

Inhale gas oxygen concentration: 100 [%]
In-trachea insert tube: Inner diameter 5 [mm]
Auxiliary supply insert tube: Inner diameter 1 [mm]
Test Condition (3)
(Using a Conventional high-frequency oscillation artificial respiration apparatus having a higher ventilation amount)
Ventilation frequency: 15 Hz
Average in-trachea pressure: 15 [cm $H_2O$] (1470 [Pa])
Ventilation amount: 30 [ml] at once
Inhale gas supply amount: 20 [l/min]
Inhale gas oxygen concentration: 100 [%]
In-trachea insert tube: Inner diameter 5 [mm]

FIG. 6 shows the test results. The partial pressure of the carbon dioxide in the blood in the artery was measured to determine how much carbon dioxide has been reduced in the blood. The normal partial pressure of the carbon dioxide in the blood is 35 to 45 [mmHg] (4655 to 5985 [Pa]). When the partial pressure of the carbon dioxide in the blood is high, it means that carbon dioxide has not been exhausted sufficiently and the ventilation in the lungs is not appropriate. When the partial pressure exceeds 45 [mmHg] (5985 [Pa]), the living body suffers from the high carbon dioxide blood symptom.

The comparison of the test results of FIG. 6 shows that even in the condition that the high carbon dioxide blood symptom is caused by the conventional high-frequency oscillation artificial respiration apparatus, the high-frequency oscillation artificial respiration apparatus 12 can maintain the partial pressure of the carbon dioxide in the artery blood in a normal range.

Furthermore, the conventional high-frequency oscillation artificial respiration apparatus cannot maintain the partial pressure of carbon dioxide in the artery blood at a normal value even when the ventilation amount is increased by 1.5 times, while the present invention enables to maintain the partial pressure of carbon dioxide in the artery blood in a normal value range with its vertilation amount at once.

As has been described above, by using the present invention, even a high-frequency oscillation artificial respiration apparatus having a small-power oscillation source (oscillating air pressure urging unit) can perform in-lungs ventilation equivalent to or more than a high-frequency oscillation artificial respiration apparatus having a large-power oscillation source. When the oscillation source is of small power, it is possible to reduce the cost of the apparatus as well as to reduce the apparatus operation noise and the apparatus size, weight, power consumption.

For example, in the case of a conventional high-frequency oscillation artificial respiration apparatus, the production of the oscillation source costs about 400000 yen, the operation noise is 53 to 56 [dB], and the current consumed is 7 to 8 [A]. In the case of a conventional high-frequency oscillation artificial respiration apparatus having a large power used in the aforementioned test condition (3), the production of the oscillation source costs about 800000 yen, the operation noise is 70 [dB] or above, and the current consumed is 13 to 14 [A]. In the conventional large-power high-frequency oscillation artificial respiration apparatus used in the test condition (3), the noise was too large and the current consumed was large.

According to the principle of the conventional method, a high-frequency oscillation artificial respiration apparatus used for grown-ups require a large-power ventilation, which causes a high level noise and a large current consumption.

A large-power high-frequency oscillation artificial respiration apparatus can perform a high-frequency oscillation ventilation with a large ventilation amount at once but this causes vibration in the lungs and may cause a load on the lungs. The high-frequency oscillation artificial respiration apparatus 12 according to the present invention can solve such a problem and improve the ventilation efficiency in the lungs as can be seen from the test results.

<Embodiment 3>

(Entire configuration of the embodiments)

Figure 7:
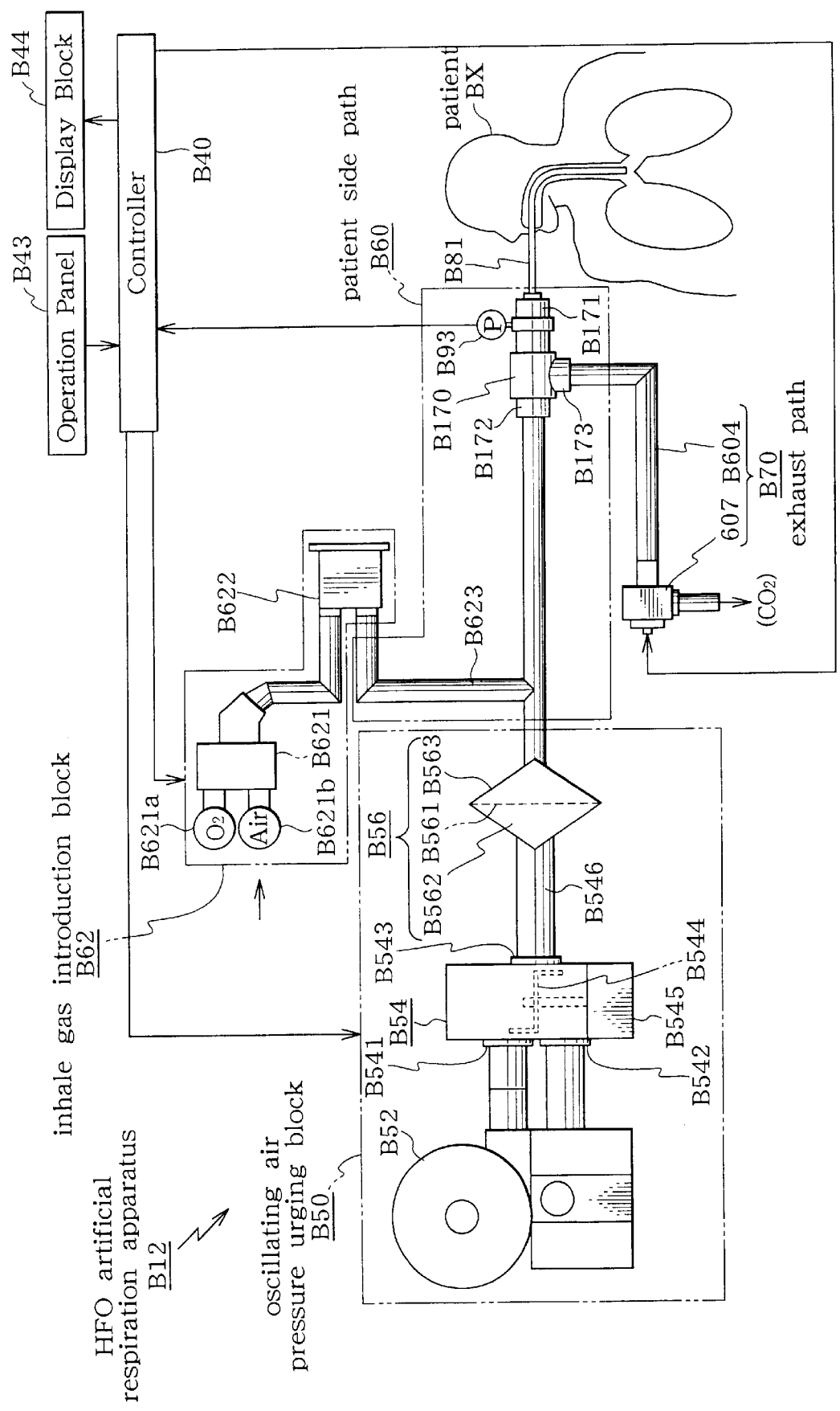
FIG. 7 is a block diagram showing a configuration of a HFO artificial respiration apparatus according to the third embodiment of the present invention.

Explanation will be given on a third embodiment of the present invention with reference to FIG. 7 to FIG. 15. FIG. 7 is a block diagram showing a configuration of a HFO artificial respiration apparatus B12 according to the present embodiment.

This HFO artificial respiration apparatus B12 includes an inhale gas introduction block B62 for supplying an inhale gas containing oxygen to a patient BX; a patient side path B60 for guiding the inhale gas from the inhale gas introduction block B62 to the patient BX; an oscillating air pressure urging block B50 for applying to the inhale gas flowing through the patient side path B60 an oscillating air pressure having a cycle shorter than the respiration cycle of the patient BX; an exhaust path B70 for exhausting an exhale gas containing carbon dioxide exhaled from the patient BX, into the atmosphere; and a controller for controlling operation of the components of the artificial respiration apparatus B12.

Description will now be directed to the respective components of the apparatus.

The blower B52 has a fan and a motor for rotating the fan. The motor includes an inverter whose rpm is controlled by the controller B40, thereby setting the air send-out amount. This air send-out amount is in proportion to a ventilation amount per one oscillation cycle. By increasing or decreasing the air send-out amount, the ventilation amount per one oscillation cycle is set.

The drive block B545 includes a motor and a reducer (not depicted) so as to rotate the rotary valve B544 at the rpm specified by the controller B40. One rotation of the rotary valve B544 makes one communication between the port B541 and the port B543 and then one communication between the port B542 and the port B543. Accordingly, an oscillating air pressure Apn of the oscillation frequency proportional to the rpm of the drive block B545 is applied to the inhale gas supplied. The controller B40 controls the rpm of the drive block B545 so as to control the oscillation frequency of the oscillating air pressure Apn.

It should be noted that the port B543 is connected to an oscillating air pressure pipe B546 for transmitting the oscillating air pressure Apn to the diaphragm mechanism B56.

Exhaust path B70 of this embodiment is same to one of the first embodiment. So it is explained for this embodiment with referring the FIG. 2. As shown in this figure, the solenoid 607d moves the movable valve by an amount according to the control signal from the controller B40. Thus, the exhale gas exhaust amount of the flow rate regulating valve 607 is automatically regulated. Since the patient side path B60 communicates with the exhaust path B70, the aforementioned regulation of the exhale gas exhaust amount also can adjust the inner pressure not only in the exhaust path B70 but also in the patient side path B60.

(Controller)

Figure 8:
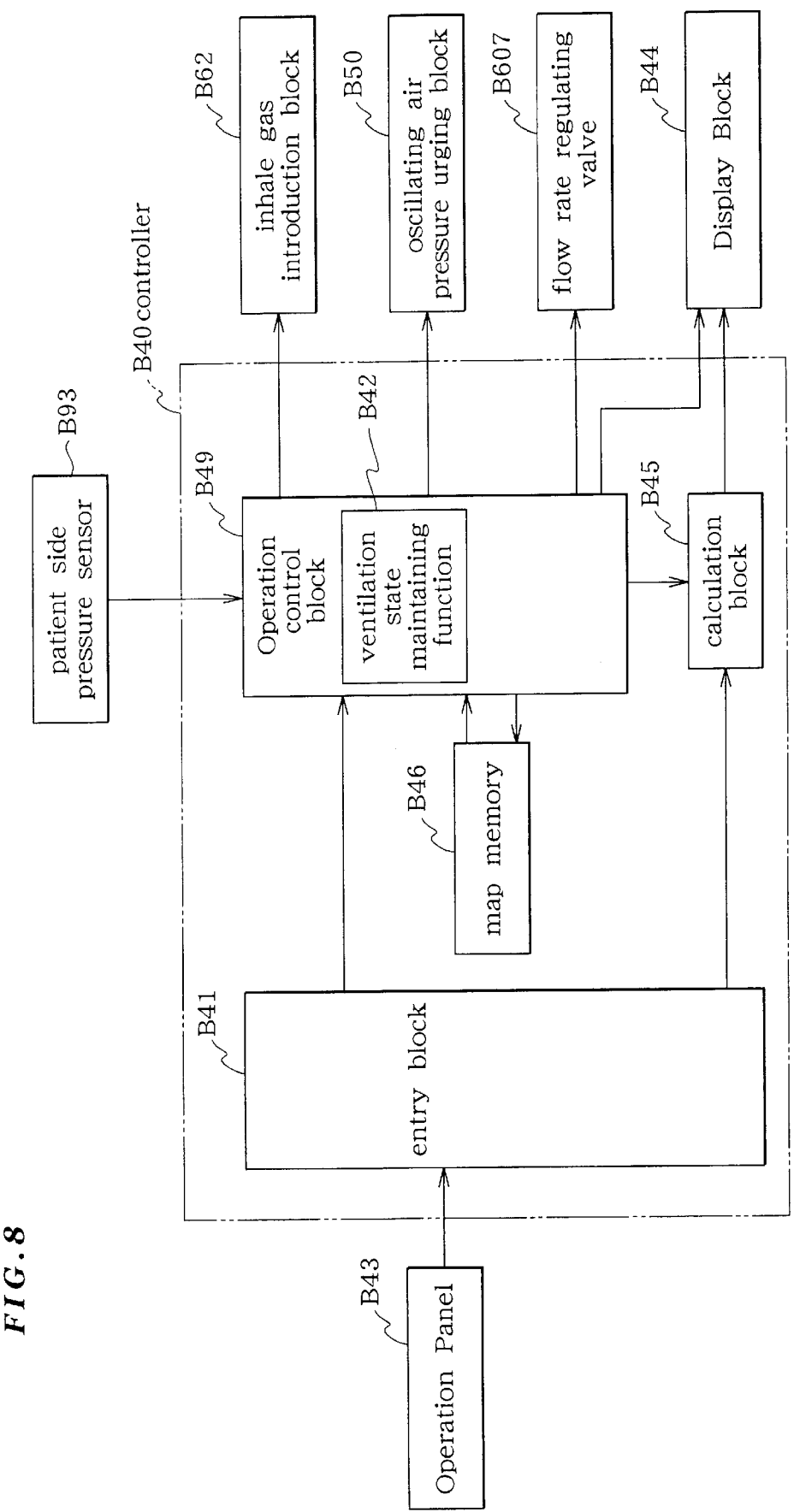
FIG. 8 is a block diagram showing a control system of the HFO artificial respiration apparatus shown in FIG. 10.

Next, explanation will be given on the controller B40 with reference to FIG. 7 and FIG. 8. FIG. 8 is a block diagram showing a control system of the HFO artificial respiration apparatus B12. The controller B40 includes a computation apparatus having a CPU, a ROM, and an A/D converter as well as a program for executing an operation control of the HFO artificial respiration apparatus which will be detailed later.

This controller B40 includes an operation panel B43 through which a doctor (operator of the HFO artificial respiration apparatus B12) enters operation conditions and a display block B44 for displaying an alveolar ventilation amount $V_A$ and the one ventilation amount $V_T$ which will be detailed later.

Furthermore, the controller B40 includes an entry block B41 for receiving an operation condition entered through the operation panel; an operation control block B49 for controlling the operations of the oscillating air pressure urging block B50, the inhale gas introduction block B62, and the flow rate regulating valve 607 (in FIG. 2) according to the operation conditions entered through the operation panel B43; a memory map B46 containing a 5-dimensional map which will be detailed later; and a calculation block B45 for calculating the palmonary alveolus ventilation amount $V_A$.

The operation panel B43 is a keyboard, for example, through which the operator (doctor) of the HFO artificial respiration apparatus B12 enters the one ventilation amount $V_T$ for the lungs of the patient BX, the oscillation of the oscillating air pressure (hereinafter, referred to as a "ventilation frequency"), the inhale gas supply amount, the average inner pressure of the patient side path, the diameter of an in-trachea insert tube B81 selected, the anatomical dead amount $V_D$, the constant K to determine the alveolar ventilation amount, and the oxygen concentration of the inhale gas.

These operation conditions entered through the operation panel B43 are all stored in the entry block B41. This entry block B41 is a memory for temporary storing. When the aforementioned operation conditions are entered, they update the previous conditions which have been stored.

Moreover, the display block B44 is, for example, a liquid crystal panel which is controlled by the operation control block B49 to display all the operation conditions entered to the entry block B49.

Next, explanation will be given on the map memory B46. This map memory B46 contains a 5-dimensional map specifying five variables, i.e., the desired one ventilation amount against the lungs of the patient BX, the ventilation frequency, the inhale gas supply amount, the average inner pressure of the patient side path B60, and the diameter of the selected in-trachea insert tube B81, thereby specifying the output of the oscillating air pressure urging block B50 (output of the drive motor of the blower B52) for realizing the desired one ventilation amount for the lungs of the patient BX.

This 5-dimensional map is constructed according to a test data obtained by measuring one ventilation amount at the tip end of the in-trachea insert tube B81 while changing the output of the oscillating air pressure urging block B50, the oscillation frequency of the oscillating air pressure, the inhale gas supply amount, the average inner pressure, and the diameter of the intrachea insert tube selected.

In other words, this 5-dimensional map has been constructed using a plenty of test data obtained as follows. The inhale gas supply amount and the average inner pressure of the patient side path B60 were changed in a plurality of stages. In each of the stages, each of the four diameters of the in-trachea insert tube B81 was applied to determine the relationship between the drive motor output of the blower B52 and the ventilation amount per cycle of the oscillating air pressure observed at the insert end of the in-trachea insert tube B81.

Accordingly, when the inhale gas supply amount, the average inner pressure of the patient side path B60, the ventilation frequency, and the diameter of the in-trachea insert tube are specified, it is possible to specify a particular test data upon the relationship between the driver motor output of the blower B52 and the ventilation amount per cycle of the oscillating air pressure observed at the insert end of the in-trachea insert tube B81.

In this embodiment, a model of lungs having a pressure sensor at the insert end of the in-trachea insert tube B81 was used to observe a ventilation amount per cycle of the oscillation air pressure as "one ventilation amount for lungs of a patient" to serve as a test data. In the HFO artificial respiration apparatus, the one ventilation amount for lungs of a patient is hardly affected by the volume and compliance of the lungs and varies depending on the inhale gas supply amount, the average inner pressure, the ventilation frequency, the amplitude of the oscillating air pressure, and the inner diameter of the in-trachea insert tube, which has been confirmed by experiments.

In the calculation block B45, an output of the blower B52 corresponding to a desired one ventilation amount is identified from a characteristic curve consisting of the aforementioned identified test data, so that the identified output is used to drive the drive motor of the blower B52, enabling to perform HFO artificial respiration with one ventilation amount desired by the operator for the lungs of the patient BX.

The 5-dimensional map will be detailed with reference to FIG. 9 to FIG. 12. These figures explain the concept of the 5-dimensional map. Firstly, the f-dimensional map has a first stage map M (FIG. 9) for specifying an inhale gas supply amount so as to specify a map $M_i$ of the next stage. The first stage map M can specify five inhale gas supply amount values. For example, when 30 [1/min] is specified for the inhale gas supply amount, $M_5$ is specified in the second stage map.

The second map $M_i$ can specify the average inner pressure of the patient side path B60 so as to specify the next stage map $M_{ij}$. (FIG. 10 shows an example of $M_5$ map.) In the second stage map $M_i$, the average inner pressure can be specified at 11 values. For example, when 10 [cm H$_2$O] (980 [Pa]) is selected for the average inner pressure in the second stage map $M_5$, $M_{56}$ is specified in the third stage map.

The third stage map $M_{ij}$ can specify a ventilation frequency of the patient side path B60 so as to specify the next stage map $M_{ijk}$. (FIG. 11 shows an example of $M_{56}$ map.) In the third stage map $M_{ij}$, five values can be specified for the ventilation frequency. For example, when 15 [Hz] is specified for the ventilation frequency in the third stage map $M_{56}$, $M_{565}$ is specified for the final stage map.

Figure 12:
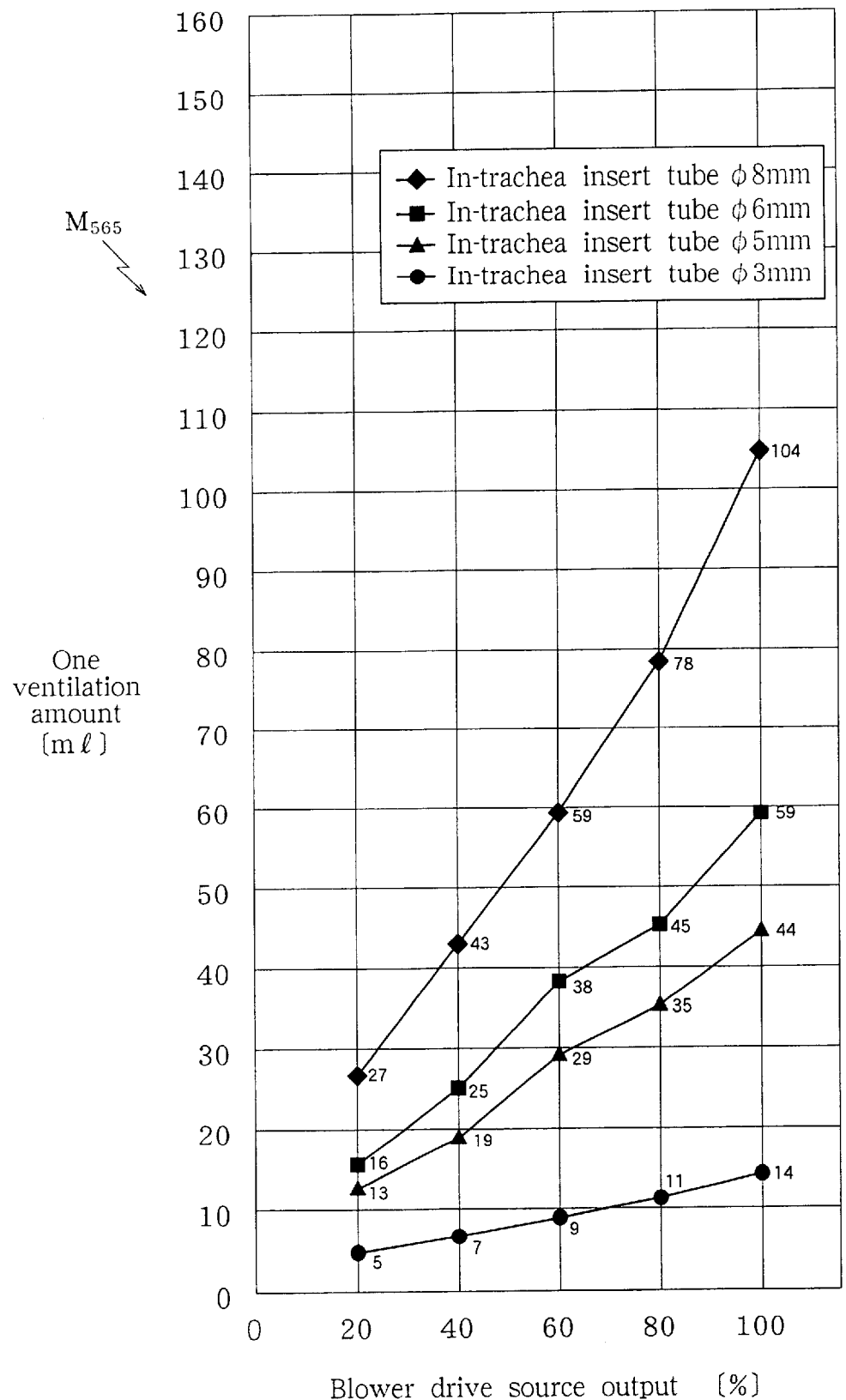
FIG. 12 explains a final stage map of the 5-dimensional map.

The final stage map $M_{ijk}$ is a test data associated with the relationship between the output of the blower B52 and the one ventilation amount for the lungs of the patient BX measured using the respective four different diameters of the in-trachea insert tube under the conditions of the inhale gas supply amount, the average inner pressure, and the ventilation frequency which have been specified in the previous stages. FIG. 12 graphically shows the concept of the final stage map M565. According to this figure, for example, when performing a HFO artificial respiration by specifying 8 [mm] for the diameter of the in-trachea insert tube B81 mounted at the end B171a of the patient side path B60 and 78 [ml] for the one ventilation amount for the lungs of the patient BX, the output of the drive motor of the blower B52 can be set to 80 [%].

The 5-dimensional map has the aforementioned configuration. Thus, by specifying the inhale gas supply amount, the average inner pressure, the ventilation frequency, the in-trachea insert tube diameter, and the desired one ventilation amount, it is possible to specify an output of the drive motor of the blower B52 for performing a HFO artificial respiration with the desired one ventilation amount. It should be noted that the parameter value intervals used in the aforementioned explanation may be reduced by collecting more test data, so that a more precise value can be specified for the one ventilation amount for the lungs of the patient BX.

Next, explanation will be given on the operation control block B49. The operation control block B49 references the oxygen concentration of the inhale gas stored in the entry block B41 and regulates the open degree of the valves at the supply sources B621a and B621b of the blender B621 of the inhale gas introduction block B62. Simultaneously with this, according to the inhale gas supply amount in the entry block B4, the open degree of the output valve of the blender B621 of the inhale gas introduction block B62 is regulated.

Moreover, the operation control block B49 references the average inner pressure stored in the entry block B41 and regulates the open degreed of the flow rate regulating valve 607 (in FIG. 2) so that the detected pressure of the patient side pressure sensor B93 is equal to a value stored.

Furthermore, when a new ventilation frequency f is entered to the entry block B41, the operation control block B49 updates the ventilation frequency f according to the ventilation frequency f entered through the operation panel B43 for the oscillating air pressure urging block B50. The operation control block B49 has a ventilation state maintaining function B42 that the product of a square of one ventilation amount $V_T$ and the ventilation frequency f is always constant. The ventilation amount value $V_T$ and the ventilation frequency f are simultaneously changed under the condition that $V_T^2 \cdot f$ is constant so as to find a target ventilation frequency to be set.

That is, if it is assumed that $f_0$ is the ventilation frequency before update, $V_{T0}$ is the one ventilation amount for the lungs of the patient, $f_1$ is the ventilation frequency updated according to the entry block 41, and $V_{T1}$ is the one ventilation amount after updated then $F_0 \cdot V_{T0}^2 = f_1 \cdot V_{T1}^2$.

Accordingly, the operation control block B49 controls the rpm of the drive block B545 of the rotary valve B54 so as to set the ventilation frequency $f_1$ and the output of the blower B52 to set the one ventilation amount $V_{T1}$ for the lungs of the patient. It should be note that the output of the blower B52 is identified according to the 5-dimensional map in the map memory B46.

Moreover, when the one ventilation amount $V_T$ for the lungs of the patient BX alone is entered to the entry block B41, the operation control block B49 controls the output of the oscillating air pressure urging block B50, i.e., the oscillating air pressure Apn to be set to the one ventilation amount $V_T$. Here also, the operation control block B49 references the aforementioned 5-dimensional map so as to identify the output of the blower B52 and set the one ventilation amount $V_T$. The operation control block B49 also displays the one ventilation amount $V_T$ which has been set. The display of the one ventilation amount $V_T$ is updated when a new one ventilation amount $V_T$ is entered of when the value has been modified by a change of the ventilation frequency f.

Next, explanation will be given on the calculation block B45. When an anatomical dead amount $V_D$ and a constant K are entered to the entry block B41, the calculation block B45 calculates the alveolar ventilation amount $V_A$ according to the equation "$V_A = K \cdot V_T^2 f / V_D$". Moreover, when no anatomical dead amount $V_D$ or no constant K are supplied from the entry block B41, an alveolar ventilation amount $V_A'$ is calculated according to a simplified equation "$V_A' = V_T^2 \cdot f$". Here, each time when the one ventilation amount $V_T$ or the ventilation amount f is changed, the alveolar ventilation amount $V_A$ or the $V_A'$ is also updated in calculation. The alveolar ventilation amount $V_A$ or $V_A'$ which has been calculated is displayed on the display block B44.

(Explanation of the principle)

Hereinafter, explanation will be given on the principle of the operation control by the aforementioned controller B40. Currently, the alveolar ventilation amount $V_A$ is used as indicating the gas convey state in the lungs and near the lungs performed by ventilation based on respiration. This alveolar ventilation amount $V_A$ varies depending on individuals. Normally, the alveolar ventilation amount $V_A$ is defined as follows taking consideration on carbon dioxide in the lungs.

$$V_A = V_{CO2} / F_{ACO2} \qquad (1)$$

wherein $V_{CO2}$ represents an amount of carbon dioxide exhaled and $F_{ACO2}$ represents a carbon dioxide concentration in the alveoli.

The aforementioned equation (1) indicates a ratio between the amount of carbon dioxide exhausted from the alveoli by ventilation and the in-blood concentration of carbon dioxide remaining in the alveoli. That is, when the alveolar ventilation amount $V_A$ is identical, the carbon dioxide concentration in the artery blood ($PaCO_2$) of the patient is unchanged and the state of the patient remains unchanged.

Here, when ventilation is performed by a normal artificial respiration apparatus instead of the HFO artificial respiration apparatus or spontaneous respiration by the patient, the one ventilation amount $V_T$ inhaled and deleted by the anatomical dead amount $V_D$ is the amount of gas which has actually reached the alveoli. Accordingly, the alveolar ventilation amount $V_A$ can be determined as follows.

$$V_A = (V_T - V_D) \times f \qquad (b\ 2)$$

wherein $V_T$ represents one ventilation amount, the $V_D$, the anatomical dead amount, and f, the ventilation frequency.

Accordingly, in an artificial respiration of not HFO type, Equation (2) is used to determine the alveolar ventilation amount $V_A$ in the initial stage ventilation state. By keeping the value unchanged while changing the ventilation frequency f and the one ventilation amount $V_T$ serving as operation parameters of HFO artificial respiration, it is possible to maintain constant the carbon oxide gas concentration in the artery blood of the patient.

In the HFO artificial respiration, ventilation is performed by a gas convey mechanism which is different from that of the normal (non-HFO) artificial respiration. Accordingly, the aforementioned Equation (2) cannot be used directly. Studies on the HFO artificial respiration have found that Equation (3) is satisfied.

$$V_A\ V_T^2 \cdot f \qquad (3)$$

This means that the alveolar ventilation amount $V_A$ is proportional to "a square of one ventilation amount ($V_T^2$)" X "ventilation frequency (f)" and can be expressed as follows.

$$V_A = K \cdot V_T^2 \cdot f / V_D \tag{4}$$

wherein K is a constant (0.13 to 0.19), $V_D$ is an anatomical dead amount, and f is a ventilation amount.

According to the aforementioned Equation (4), when the "one ventilation amount $V_T$" and the "ventilation frequency f" serving as operation parameters of the artificial respiration apparatus are changed while keeping constant the alveolar ventilation amount $V_A$ at the initial stage state, the gas convey amount stays unchanged. That is, the gas exchange in the alveolar level also stays unchanged. Thus, it is possible to maintain constant the carbon dioxide concentration in the artery blood of the patient.

Moreover, when it is not easy to determine the constant K and the to determine the alveolar ventilation amount may be simplified into Equation (5), considering the relationship of Equation (3).

$$V_A' = V_T^2 f \tag{5}$$

Figure 13:
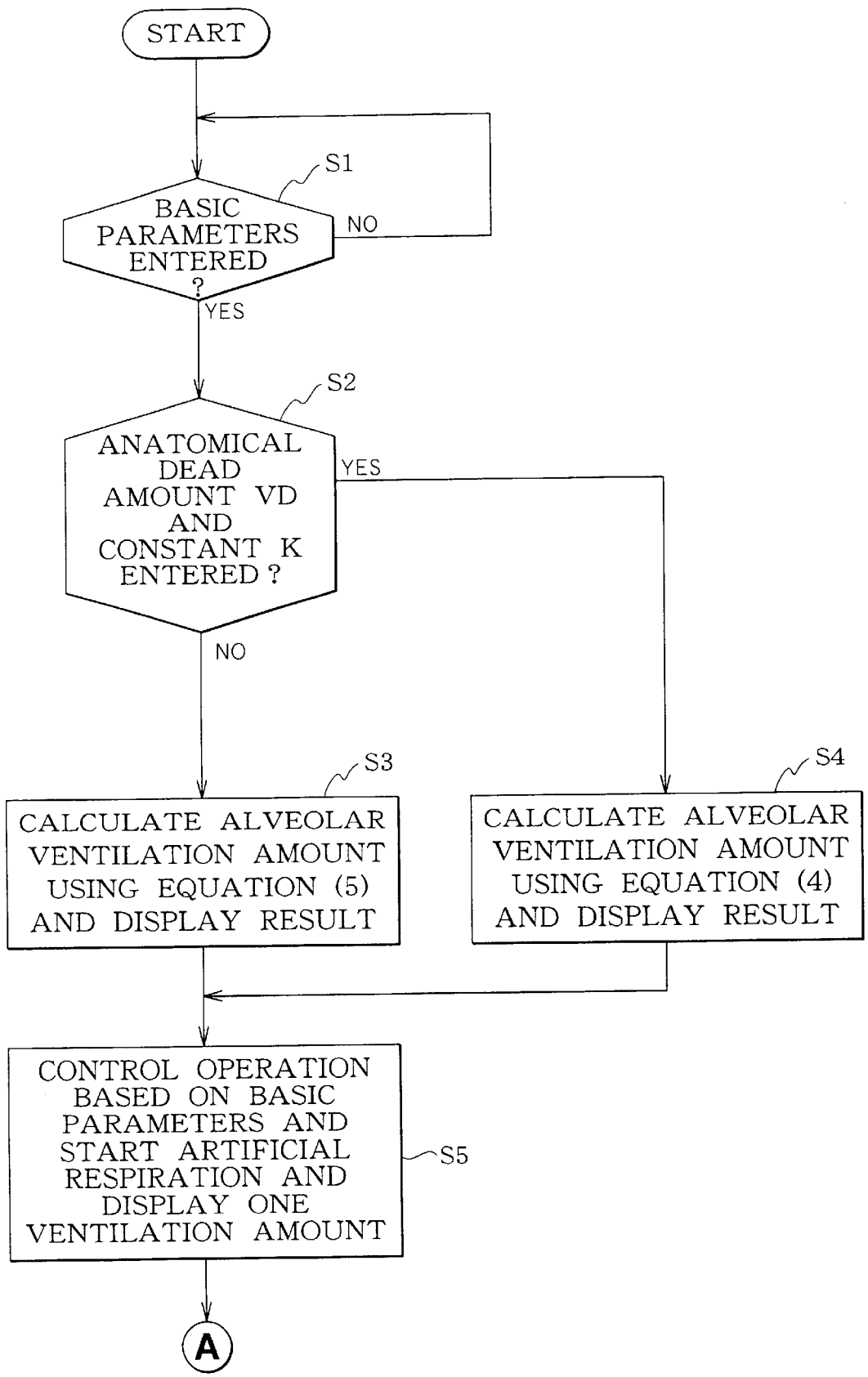
FIG. 13 is a flowchart showing operation of the HFO artificial respiration apparatus.
Figure 14:
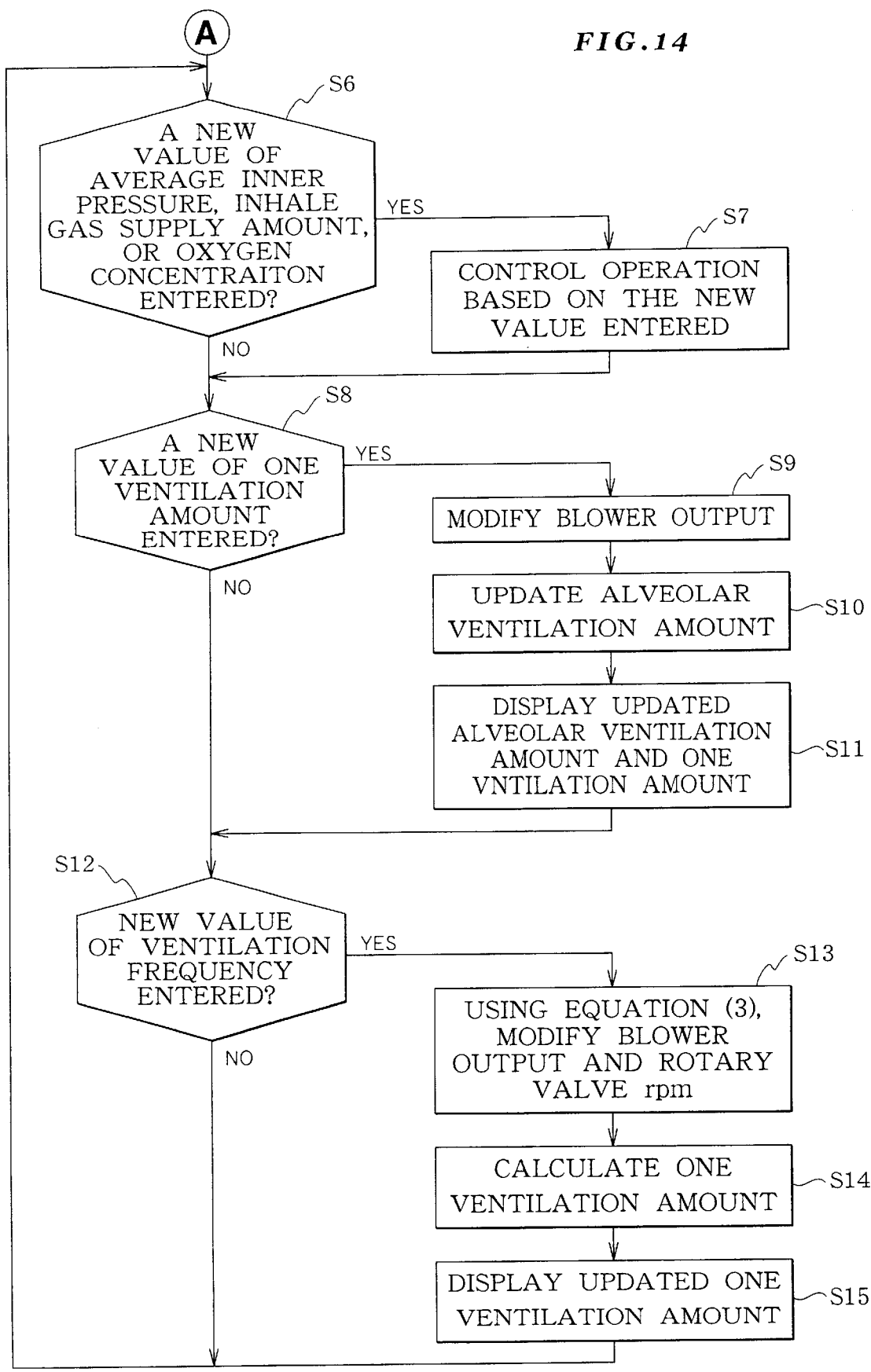
FIG. 14 is a flowchart of the operation to be continued after the operation of FIG. 13.

Together with the operation control by the controller B40, the operation of the entire HFO artificial respiration apparatus B12 will be explained with reference to FIG. 2, FIG. 7, FIG. 8, FIG. 13 and FIG. 14. FIG. 13 is a flowchart showing the operation of the HFO artificial respiration apparatus B12, and FIG. 14 is a flowchart to be continued after the operation of FIG. 13.

Firstly, the doctor enters basic parameters through the operation panel B43 according to the age, weight, and state of the patient BX: the ventilation frequency f of the oscillating air pressure Apn, the one ventilation amount $V_T$, the average inner pressure of the patient side path B60, the inner diameter of the in-trachea insert tube used, the inhale gas supply flow rate, and the inhale gas oxygen concentration.

Moreover, the doctor further enters through the operation panel B43 the anatomical dead amount $V_D$ of the lungs of the patient BX and the constant K to obtain the alveolar ventilation amount $V_A$ if they are known by a preceding inspection.

In the controller B40 of the HFO artificial respiration apparatus B12, the entry block B41 stores the aforementioned basic parameters entered as well as the anatomical dead amount $V_D$ of the lungs of the patient BX and the constant K to be used to determine the alveolar ventilation amount $V_A$, if they have been entered.

In the controller B40, step S1 checks whether the basic parameters have been entered and if Yes, step S2 checks whether the anatomical dead amount $V_D$ and the constant K have been entered.

If the anatomical dead amount $V_D$ and the constant K have not been entered, the calculation block B45 calculates the alveolar ventilation amount $V_A'$ using the aforementioned Equation (5), and the calculation result is displayed on the display block B44 (step S3). Moreover, if the anatomical dead amount $V_D$ and the constant K have been entered, the calculation block B45 calculates the alveolar ventilation amount $V_A$ using the aforementioned Equation (4), and the calculation result is displayed on the display block B44 (step S4).

The operation control block B49 references and the entry block B41 and performs operation control according to the basic parameters entered (step S5). That is, the valve open degrees of the supply sources B621a and B621b are adjusted so the inhale oxygen concentration is identical to the entered value, and an output valve having the inhale gas supply flow rate specified is selected and opened.

Moreover, the operation control block B49 controls the rotary valve B54, i.e., rpm of the motor of the drive block B545 so that the ventilation frequency f is at a value specified. Furthermore, the operation control block B49 controls the rpm of the drive motor of the blower B52 so that the one ventilation amount $V_T$ is as is at a value specified. Moreover, the operation control block B49 controls the flow rate regulating valve 607 so that its open degree results in the average inner pressure specified is detected by the patient side pressure sensor B93.

Furthermore, the operation control block B49 displays on the display block B44 the one ventilation amount $V_T$ which has been entered.

The HFO artificial respiration apparatus B12 is set up by the aforementioned operation control. An inhale gas is supplied from the inhale gas introduction block 62 to pass through the patient side path B60 to the patient BX. Furthermore, the oscillating air pressure Apn is applied from the oscillating air pressure urging block B50 to the inhale gas flowing through the patient side path B60. The inhale gas is divided in the branching pipe B170 to the patient BX side and the exhaust path B70. The inhale gas which has flown into the side of the patient BX is fed by the positive pressure of the oscillating air pressure Apn through the in-trachea insert tube B81 into the lungs of the patient BX, thus supplying oxygen to the lungs. Moreover, an exhale gas containing carbon dioxide generated in the lungs is sent by the negative pressure of the oscillating air pressure Apn through the in-trachea insert tube B81 into the branching pipe B170 and is pushed into the exhaust path B70 together with the subsequent inhale gas so as to be exhausted into the atmosphere.

As has been described above, after the artificial respiration is started by the HFO artificial respiration apparatus B12, according to the state of the patient BX, the doctor enters new values to update the HFO parameters: one ventilation amount $V_T$, ventilation frequency f, average inner pressure, inhale gas supply amount, and inhale gas oxygen concentration.

If one of the parameters of the average inner pressure, the inhale gas supply amount, and the inhale gas oxygen concentration is entered (step S6), the operation control block B49 performs the aforementioned operation control and sets the new operation condition (step S7).

Moreover, when a new value of the one ventilation amount $V_T$ is entered (step S8), the operation control block B49 performs the aforementioned control to set the blower B52 to the new one ventilation amount $V_T$ (step S9). Thus, when the one ventilation amount $V_T$ alone is modified without changing the ventilation frequency f, the alveolar ventilation amount $V_A'$ (or $V_A$) is also changed. Accordingly, the calculation block B45 uses the Equation (5) (or Equation (4) if the anatomical dead amount $V_D$ and the constant K have been entered) to calculate a new alveolar ventilation amount $V_A'$ (or $V_A$) (step S10) and displays the calculation result on the display block B45 (step S11).

Moreover, if a new value of the ventilation frequency f is entered (step S12), then the operation control block B49 uses the ventilation state maintaining function B42 to change the one ventilation amount $V_T$ according to the change of the ventilation frequency f. That is, the blower output and the rotary valve rpm are simultaneously changed so that the value of $V_T^2 \cdot f$ is constant (step S13).

The aforementioned operation control will be explained using specific values. If the one ventilation amount is 100 [ml] and the ventilation frequency is 15 [Hz], the alveolar ventilation amount $V_A'$ is calculated by the calculation block B45 using the Equation (5) to obtain Equation (6) as follows.

$$V_A' = V_T^2 \cdot f = 100^2 \times 15 = 150000 \tag{6}$$

When it is desired to change the ventilation frequency f to 9 [Hz] from the aforementioned state, the one ventilation amount $V_T$ to maintain the alveolar ventilation amount $V_A'$ can be calculated from the Equation (7) as follows.

$$V_T = (V_A/f)^{1/2} = (150000/9)^{1/2} = 129.1 \approx 130 \quad (7)$$

Figure 15:
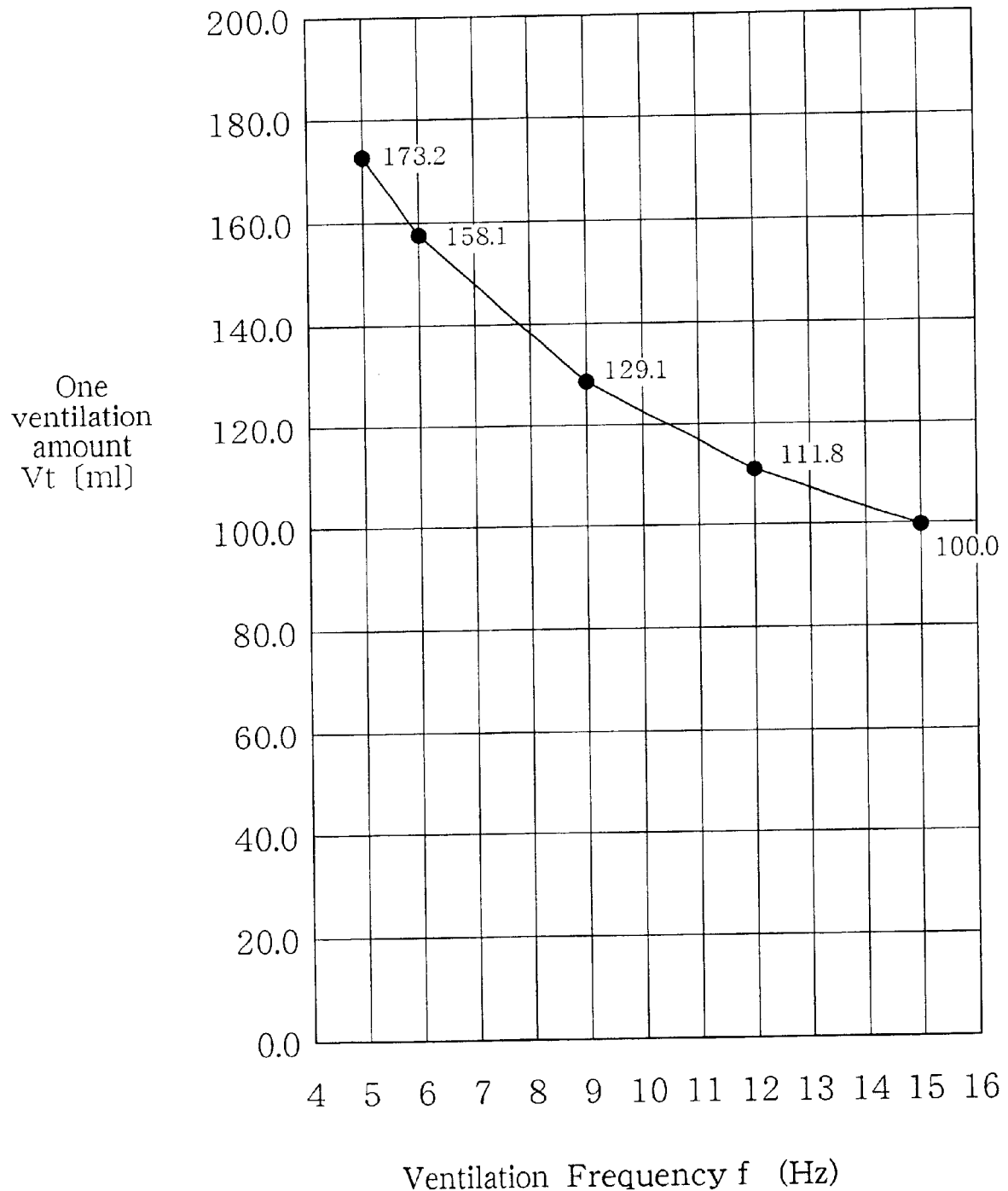
FIG. 15 graphically shows a change of the one ventilation amount $V_T$ for maintaining the alveolar ventilation amount $V_A' = 150000$ when the ventilation frequency f is changed.

Accordingly, when the ventilation frequency f is changed from 15 [Hz] to 9 [Hz], the ventilation amount VT is also controlled to be changed from 100 [ml] to 130 [ml]. Here, as an example, FIG. 15 shows a change of the one ventilation amount $V_T$ for maintaining the alveolar ventilation amount $V_A'$ while the ventilation frequency f is changed.

The operation control block B49 performs the aforementioned control and the one ventilation amount $V_T$ updated by the control is output from the calculation block B45 (step S14) and displayed at the display block B44 (step 15).

Thus, in the HFO artificial respiration apparatus B12, various parameters are entered when required according to the change of the state of the patient BX and control is performed according to the parameters entered, so as to continue the HFO artificial respiration while controlling the operation.

As has been described above, in this embodiment, the operation control block B49 has the ventilation change maintaining function B42 and accordingly, upon change of the ventilation frequency f, the one ventilation amount $V_T$ is updated so as to maintain the $V_T^2 \cdot f$ constant. Thus, when the ventilation frequency f is changed, the alveolar ventilation amount $V_A$ can be maintained at a constant value, thus enabling to evade occurrence of a sudden change of the carbon dioxide concentration in the blood.

Thus, it is possible to reduce the interaction between the two parameters which determine the partial pressure of the carbon dioxide in the blood, to evade a sudden change of the ventilation state in the patient, and to simplify the setting of the ventilation frequency f.

Moreover, the controller B40 is provided with the display block B44 for displaying the alveolar ventilation amount $V_A$ calculated by the calculation block B45. The doctor can perform the HFO artificial respiration while observing the alveolar ventilation amount $V_A$ serving as a criteria of the ventilation state in the patient BX. That is, the doctor operating the HFO artificial respiration apparatus B112 can set an appropriate ventilation condition.

In the aforementioned HFO artificial respiration apparatus B12, when the ventilation frequency is modified, the operation control is performed so as to simultaneously change the one ventilation amount according to the Equation (3). However, the present invention is not to be limited to this. For example, it is also possible to provide an apparatus in which the ventilation frequency can be changed in two modes: first mode in which the ventilation frequency alone is changed and a second mode in which the ventilation frequency is changed together with the one ventilation amount, so that the operation control block 49 performs the operation of a selected mode.

Moreover, calculation of a new one ventilation amount to be set according to a change of the ventilation frequency can be calculated by the calculation block B45 so that the calculation result is output to the operation control block B49.

In this case, the operation control may be performed so that the display block B44 displays a difference between the ventilation frequency values before and after modification and a difference between the one ventilation amount value before and after modification.

As has been described above, the apparatus disclosed in claim 1 includes an auxiliary inhale gas supply block for supplying an inhale gas into the lungs of the patient through a path different from the patient side path. That is, an inhale gas is actively supplied into the lungs of the patient apart from the ventilation by the high-frequency oscillation. Accordingly, it is possible to sufficiently perform ventilation in the lungs and maintain a sufficient oxygen concentration without increasing the amplitude of the oscillating air pressure. Accordingly, it is possible to effectively evade generation of a load on the lungs of the patient caused by a high or low pressure state and to maintain a preferable artificial respiration.

Moreover, since the amplitude of the oscillating air pressure can be reduced, it is possible to suppress vibration of the breast of the patient and affects to the other medical instrument or measurement instrument.

Furthermore, since the pressure amplitude can be reduced, it is possible to reduce the output of the oscillating air pressure urging unit or replace the oscillating air pressure urging unit with one having a lower output. This enables to reduce the noise and current consumption as well as to reduce the apparatus size and weight.

The apparatus disclosed in claim 2 is characterized in that the inhale gas supply source of the auxiliary inhale gas supply block is shared by the inhale gas introduction block. This eliminates need of an independent inhale gas supply source, thus increasing the apparatus productivity and reducing the apparatus size and weight.

The apparatus disclosed in claim 3 is characterized in that the auxiliary inhale gas supply block includes an auxiliary supply insert tube which is connected to the patient side end of the auxiliary inhale gas supply path. Accordingly, it is possible to send the inhale gas directly to the depth of the lungs of the patient, improving the ventilation efficiency.

In the apparatus disclosed in claim 4, the auxiliary supply insert tube and the in-trachea insert tube are formed as a unitary block having a configuration not mixing the gases contained in each of the tubes. Accordingly, it is possible to smoothly insert the tubes into the trachea of the patient and the inhale gas supplied from the auxiliary supply insert tube contributes to an effective ventilation in the lungs before being exhausted through the in-trachea insert tube.

In the apparatus disclosed in claim 5, the auxiliary inhale gas supply block includes an intermittent inhale gas supply unit for regulating an inhale gas flow in the auxiliary inhale gas supply path at a constant cycle repeated. Accordingly, the inhale gas supply from the auxiliary inhale gas supply path repeats an intermittent discharge, which increases the oxygen diffusion in the lungs and enhances the ventilation efficiency.

The apparatus disclosed in claim 6 includes an auxiliary path humidifying unit. Accordingly, it is possible to humidify the inhale gas flowing in the auxiliary inhale gas supply path. This prevents drying in the lungs and perform an artificial respiration in a preferable condition.

In the apparatus disclosed in claim 7, the auxiliary inhale gas supply block includes a chemical liquid supply unit. Accordingly, it is possible to supply a chemical liquid into the auxiliary inhale gas supply path as is required while maintaining a high-frequency oscillation artificial respiration. Thus, it is possible to effectively cure the patient.

The apparatus disclosed in claim 8 includes a first regulating unit and a second regulating unit. Accordingly, it is possible to separately regulate an oxygen concentration and a flow rate of the inhale gas flowing through the patient side path and a flow rate of the inhale gas flowing through the auxiliary inhale gas supply path. Thus, it is possible to accurately regulate the ventilation efficiency according to the state of the patient and smoothly adjust the pressure in the lungs.

The apparatus disclosed in claim 9 includes a first flow rate controller for controlling, according to an output from the pressure sensor, the first regulating unit. This enables to suppress an excessive increase or decrease of the inhale gas pressure, so as to perform an artificial respiration without applying a load to the patient. Moreover, the inhale gas flow rate and the inhale gas pressure can automatically be adjusted without operation by the user.

The apparatus disclosed in claim 10 includes a second flow rate controller for controlling, according to an output from the pressure sensor, the second regulating unit. This enables to suppress an excessive increase or decrease of the inhale gas pressure and to perform an artificial respiration without applying a load to the patient. Moreover, it is possible to automatically adjust the flow rate and the inhale gas pressure without operation by the user.

The apparatus disclosed in claim 11 includes a valve controller for controlling, according to an output from the pressure sensor, an inhale gas flow rate of the flow rate regulating valve. This enables to suppress an excessive increase or decrease of the inhale gas pressure and to perform an artificial respiration without applying a load to the patient. Moreover, it is possible to automatically regulate the inhale gas flow rate and the inhale gas pressure without operation by the user.

The present invention having the aforementioned configuration can provide an excellent high-frequency oscillation artificial respiration apparatus which has not been obtained in the conventional technique.

Moreover, the operation control block has the ventilation state maintaining function, so that upon change of the ventilation frequency f, the ventilation amount $V_T$ per oscillation cycle is simultaneously changed so as to maintain a constant value of $V_T^2 \cdot f$. Accordingly, upon setting modification of the ventilation frequency f, it is possible to maintain the alveolar ventilation amount $V_A$ at a constant value, which evades a sudden change in the carbon dioxide concentration in the blood.

This enables to reduce interaction between the two parameters which determine the partial pressure of carbon dioxide in the blood, to evade a sudden change of the ventilation state in the patient upon setting modification of the oscillation frequency, and to simplify the setting modification of the oscillation frequency.

Moreover, when the controller is provided with a display block for displaying the alveolar ventilation amount $V_A$ calculated by the calculation block, the doctor can perform HFO artificial respiration while observing the alveolar ventilation amount serving as a criteria of the ventilation state in the patient. The operator (doctor) of the HFO artificial respiration apparatus can set an appropriate ventilation condition.

The present invention having the aforementioned configuration can provide an excellent HFO artificial respiration apparatus which has not been available.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein. The entire disclosure of Japanese Patent Application No. 11-309447 (filed on Oct. 29$^{th}$, 1999) and Japanese Patent Application No. 11-363696 (filed on Dec. 22, 1999) including specification, claims, drawings and summary are incorporated herein by reference in its entirety.

What is claimed is:

1. A high-frequency oscillation artificial respiration apparatus comprising:

an inhale gas introducer that supplies an inhale gas containing oxygen to a patient, a patient side path that guides the inhale gas from the inhale gas introducer into the patient, an oscillating air pressure provider that applies an oscillating air pressure, having a higher frequency than a respiration frequency of the patient, to the inhale gas flowing through the patient side path, and an exhaust path that exhausts an exhale gas containing carbon dioxide exhaled from the patient, into the atmosphere, wherein the patient side path comprises a branching pipe that branches a flow from the inhale gas introducer to the exhaust path side and the patient side and an in-trachea insert tube which is connected to the patient side end of the branching pipe and can be inserted through a mouth into the trachea of the patient, the apparatus further comprising an auxiliary inhale gas supply that supplies an inhale gas to the vicinity of the lungs of the patient through a path different from the patient side path, the auxiliary inhale gas supply including an inhale gas supply including an inhale gas supply source and an auxiliary inhale gas supply path, which is different from the patient side path, that guides the inhale gas from the supply source into the lungs of the patient.

2. A high-frequency oscillation artificial respiration apparatus as claimed in claim 1, wherein the inhale gas supply source of the auxiliary inhale gas supply is shared by the inhale gas introducer, and the auxiliary inhale gas supply path, which is different from the patient side path, guides the inhale gas generated in the inhale gas introducer, into the lungs of the patient.

3. A high-frequency oscillation artificial respiration apparatus as claimed in claim 1, wherein the auxiliary inhale gas supply comprises an auxiliary supply insert tube which is connected to the patient side end of the auxiliary inhale gas supply path and can be inserted into the trachea of the patient.

4. A high-frequency oscillation artificial respiration apparatus as claimed in claim 3, wherein the auxiliary supply insert tube and the in-trachea insert tube are formed as a unitary device having a configuration that prevents mixing the gases contained in each of the tubes.

5. A high-frequency oscillation artificial respiration apparatus as claimed in claim 1, wherein the auxiliary inhale gas supply comprises an intermittent inhale gas supply unit that regulates an inhale gas flow in the auxiliary inhale gas supply path at a constant repeat cycle.

6. A high-frequency oscillation artificial respiration apparatus as claimed in claim 1, wherein the auxiliary inhale gas supply comprises an auxiliary path humidifying device that humidifies the inhale gas flowing in the auxiliary inhale gas supply path.

7. A high-frequency oscillation artificial respiration apparatus as claimed in claim 1, wherein the auxiliary inhale gas supply includes a chemical liquid supply unit that supplies a chemical liquid into the auxiliary inhale gas supply path.

8. A high-frequency oscillation artificial respiration apparatus as claimed in claim 1, the apparatus further comprising:

a first regulator that regulates an oxygen concentration and a flow rate of the inhale gas flowing through the patient side path, and a second regulator that regulates an oxygen concentration and a flow rate of the inhale gas flowing through the auxiliary inhale gas supply path.

9. A high-frequency oscillation artificial respiration apparatus as claimed in claim 8, the apparatus further comprising:

a pressure sensor that detects a pressure in the vicinity of the lungs of the patient, and a first flow rate controller that controls, according to an output from the pressure sensor, the first regulator to adjust the flow rate of the inhale gas flowing in the patient side path.

10. A high-frequency oscillation artificial respiration apparatus as claimed in claim 8, the apparatus further comprising:

a pressure sensor that detects a pressure in the vicinity of the lungs of the patient, and a second flow rate controller that controls, according to an output from the pressure sensor, the second regulator to adjust the flow rate of the inhale gas flowing in the auxiliary inhale gas supply path.

11. A high-frequency oscillation artificial respiration apparatus as claimed in claim 1, the apparatus further comprising:

a flow rate regulating valve provided in the exhaust path for regulating a flow rate of the exhale gas, a pressure sensor that detects a pressure in the vicinity of the lungs of the patient, and a valve controller that controls, according to an output from the pressure sensor, an opening amount of the flow rate regulating valve.

12. A high-frequency oscillation (HFO) artificial respiration apparatus comprising:

an inhale gas introducer that supplies an inhale gas containing oxygen to a patient;

a patient side path that guides the inhale gas from the inhale gas introducer to the patient;

an oscillating air pressure provider that provides the inhale gas flowing in the patient side path with an oscillating air pressure having a cycle shorter than a respiration cycle of the patient, the oscillating air pressure provider comprising a diaphragm mechanism including a film member that provides an oscillating air pressure to an inhale gas;

an exhaust path that exhausts into the atmosphere an exhale gas containing carbon dioxide exhaled from the patient; and a controller that controls operation of the oscillating air pressure provider, wherein the oscillating air pressure provider regulates a ventilation amount per oscillation cycle and an oscillating frequency of the oscillating air pressure, the controller includes an entry device that accepts the oscillation frequency entered, and an operation controller that controls the oscillating air pressure provider to supply an output oscillating air pressure set to the oscillation frequency entered, and the operation controller has a ventilation state maintaining function that modifies the oscillation frequency according to an entered value, the oscillation controller modifying a ventilation amount per oscillation cycle and an oscillation frequency of the oscillating air pressure such that a value of $V_T^2 \cdot f$ is maintained constant, where $V_T$ represents a ventilation amount per oscillation cycle for lungs of the patient and f represents an oscillation frequency.

13. A high-frequency oscillation artificial respiration apparatus as claimed in claim 12, wherein the entry device also enters a ventilation amount for lungs of the patient, and the operation controller controls the oscillating air pressure provider to be set at the ventilation amount entered.

14. A high-frequency oscillation artificial respiration apparatus as claimed in claim 12, wherein the patient side path is provided with an inner pressure regulator that regulates an average inner pressure of the patient side path, the entry device accepts an input of an average inner pressure, and the operation controller controls the inner pressure regulator according to the average inner pressure entered.

15. A high-frequency oscillation artificial respiration apparatus a claimed in claim 12, wherein the entry device accepts inputs of an anatomical dead amount $V_D$ and a constant K of lungs of the patient, the controller includes a calculator that calculates an alveolar ventilation amount $V_A$ defined by equation $V_A = K \cdot V_T^2 \cdot V_D$, and the controller is provided with a display that displays the alveolar ventilation amount $V_A$ calculated.

* * * * *

UNITED STATES PATENT AND TRADEMARK OFFICE
CERTIFICATE OF CORRECTION

PATENT NO. : 6,557,554 B1
DATED : May 6, 2003
INVENTOR(S) : Y. Sugiura

It is certified that error appears in the above-identified patent and that said Letters Patent is hereby corrected as shown below:

Title page,
Item [56], References Cited, U.S. PATENT DOCUMENTS, should be added:
-- 5,092,326   3/03/92      Winn et al.
5,007,420      4/16/91      Bird
5,862,802      1/26/99      Bird
4,543,951      10/1/85      Phuc -- and
FOREIGN PATENT DOCUMENTS, should be added:
-- 2105594     03/30/83     United Kingdom
0234736        09/02/87     EPO --

Column 28,
Line 45, "$V_A = K \cdot V_T^2 \cdot V_D$" should be -- $V_A = K \cdot V_T^2 \cdot f/V_D$ --.

Signed and Sealed this

Twenty-third Day of March, 2004

JON W. DUDAS
*Acting Director of the United States Patent and Trademark Office*